United States Patent [19]
Abramson et al.

[11] Patent Number: 5,674,738
[45] Date of Patent: Oct. 7, 1997

[54] DNA ENCODING THERMOSTABLE NUCLEIC ACID POLYMERASE ENZYME FROM THERMUS SPECIES Z05

[75] Inventors: Richard D. Abramson; David H. Gelfand, both of Oakland; L. Lawrence Greenfield, Pleasant Hill, all of Calif.

[73] Assignee: Roche Molecular Systems, Inc., Branchburg, N.J.

[21] Appl. No.: 520,422

[22] Filed: Aug. 29, 1995

Related U.S. Application Data

[62] Division of Ser. No. 113,531, Aug. 27, 1993, Pat. No. 5,455,170, which is a continuation of Ser. No. 590,466, Sep. 28, 1990, abandoned, which is a continuation-in-part of Ser. No. 523,394, May 15, 1990, Pat. No. 5,079,352, which is a continuation-in-part of Ser. No. 143,441, Jan. 12, 1988, abandoned, which is a continuation-in-part of Ser. No. 63,509, Jun. 17, 1987, Pat. No. 4,889,818, which is a continuation-in-part of Ser. No. 899,241, Aug. 22, 1986, abandoned.

[51] Int. Cl.$^6$ .............................. C12N 9/12; C12N 15/54
[52] U.S. Cl. .................. 435/252.3; 536/23.2; 435/320.1; 435/252.33; 435/419; 435/325
[58] Field of Search ...................... 536/23.2; 435/320.1, 435/252.33, 252.3, 419, 325, 194

[56] References Cited

U.S. PATENT DOCUMENTS

| | | | |
|---|---|---|---|
| 4,889,818 | 12/1989 | Gelfand et al. | 435/194 |
| 4,965,188 | 10/1990 | Mullis et al. | 435/6 |
| 5,374,553 | 12/1994 | Gelfand et al. | 435/252.3 |

FOREIGN PATENT DOCUMENTS

| | | |
|---|---|---|
| 8906691 | 7/1989 | WIPO |

OTHER PUBLICATIONS

Chien et al., 1976, "Deoxyribonucleic Acid Polymerase From the Extreme Thermophile *Thermus aquaticus*" J. Bacteriology 127(3):1550–1557.

Degryse et al., 1978, "A Comparative Analysis of Extreme Thermophilic Bacteria Belonging to the Genus Thermus" Arch. Microbiol. 117:189–196.

Kaledin et al., 1980, "Isolation and Properties of DNA Polymerase From Extremely Thermophilic Bacterium *Thermus aquaticus* YT1" 45(4):494–501.

Degryse et al., 1981, "Studies on the Central Metabolism of Thermus Aquaticus an Extreme Thermophilic Bacterium Anaplerotic Reactions and Their Regulation" Arch. Microbiol. 129:173–177.

Suggs et al., 1981, "Use of Synthetic Oligonucleotides as Hybridization Probes: Isolation of Cloned cDNA Sequences for Human Beta2–Microglobulin" Proc. Natl. Acad. Sci. USA 78(11):6613–6617.

Young et al., 1983, "Efficient Isolation of Genes by Using Antibody Probes" Proc. Natl. Acad. Sci. USA 80:1194–1198.

Microbiology, 5th Ed., 1986, pp. 41–49, ed M.J. Pelczal, Jr. et al., published by McGraw–Hill Book Company (New York) "The Characterization, Classification and Identification of Microorganisms".

Williams, R.A.D., "Biochemical Taxonomy of the Genus Thermus", published in: Microbiology of Extreme and its Potential for Biotechnology, pp. 82–97, eds., M.S. DaCoast, J.C. Durate and R.A.D. Williams, a volume of The Proceedings of the Federation of Eurpoean Microbiological Societies Symposium held in Troia, Portugal, 18–23 Sep. 1988, published by Elsevier Applied Science (London and New York).

Bernad et al., 1989, "A Conserved 3'–5' Exonuclease Active Site in Prokaryotic and Eukaryotic DNA Polymerases" Cell 59:219–228.

Gelfand, D.H., PCR Technology, Principles and Applications for DNA Amplification, Chapter 2, Entitled "Taq DNA Polymerase" pp. 17–22 (1989), Ed. by H.A. Erlich.

Laywer et al., 1989, "Isolation, Characterization, and Expression in *Escherichia coli* of the DNA Polymerase Gene from *Thermus aquaticus*" J. Biol. Chem. 264(11):6427–6437.

Leavitt and Ito, 1989, "T5 DNA Polymerase: Structural–Functional Relationships to Other DNA Polymerases" Proc. Natl. Acad. Sci. USA 86:4465–4469.

Microbiology, 4th Ed., 1990, pp. 11–19, edited by B.D. Davis et al., published by J.B. Lippincott Company (Philadelphia) "Evolution of Microbiology and of Microbes".

*Primary Examiner*—Keith D. Hendricks
*Attorney, Agent, or Firm*—George W. Johnston; Patricia S. Rocha-Tramaloni; Stacey R. Sias

[57] ABSTRACT

A purified thermostable enzyme is derived from the eubacterium Thermus species Z05. The enzyme has DNA polymerase, activity reverse transcriptase activity, and optionally 5'→3' exonuclease activity. The enzyme can be native or recombinant, and may be used with primers and nucleoside triphosphates in a temperature-cycling chain reaction where at least one nucleic acid sequence is amplified in quantity from an existing sequence.

17 Claims, No Drawings

DNA ENCODING THERMOSTABLE NUCLEIC ACID POLYMERASE ENZYME FROM THERMUS SPECIES Z05

CROSS-REFERENCE TO RELATED APPLICATIONS

This application is a divisional of application Ser. No. 08/113,531, filed Aug. 27, 1993 now U.S. Pat. No. 5,455, 170, which is a Continuation of Ser. No. 07/590,466, filed Sep. 28, 1990, now abandoned, which is a Continuation in Part of Ser. No. 07/523,394, filed May 15, 1990, now U.S. Pat. No. 5,079,352, which is a Continuation in Part of Ser. No. 07/143,441, filed Jan. 12, 1988, now abandoned, which is a Continuation in Part of Ser. No. 07/063,509, filed Jun. 17, 1987, now U.S. Pat. No. 4,889,818, which is a Continuation in Part of Ser. No. 06/899,241, filed Aug. 22, 1986, now abandoned.

BACKGROUND OF THE INVENTION

1. Field of the Invention

The present invention relates to a purified, thermostable DNA polymerase purified from the thermophilic bacteria Thermus species Z05 and means for isolating and producing the enzyme. Thermostable DNA polymerases are useful in many recombinant DNA techniques, especially nucleic acid amplification by the polymerase chain reaction (PCR).

2. Background Art

Extensive research has been conducted on the isolation of DNA polymerases from mesophilic microorganisms such as E. coli. See, for example, Bessman et al., 1957, *J. Biol. Chem.* 223:171-177, and Buttin and Kornberg, 1966, *J. Biol. Chem.* 241:5419-5427.

Much less investigation has been made on the isolation and purification of DNA polymerases from thermophiles such as Thermus species Z05. Kaledin et al., 1980, *Biokhymiya* 45:644-651, disclose a six-step isolation and purification procedure of DNA polymerase from cells of Thermus aquaticus YT-1 strain. These steps involve isolation of crude extract, DEAE-cellulose chromatography, fractionation on hydroxyapatite, fractionation on DEAE-cellulose, and chromatography on single-strand DNA-cellulose. The molecular weight of the purified enzyme is reported as 62,000 daltons per monomeric unit.

A second purification scheme for a polymerase from Thermus aquaticus is described by Chien et al., 1976, *J. Bacteriol.* 127:1550-1557. In this process, the crude extract is applied to a DEAE-Sephadex column. The dialyzed pooled fractions are then subjected to treatment on a phosphocellulose column. The pooled fractions are dialyzed and bovine serum albumin (BSA) is added to prevent loss of polymerase activity. The resulting mixture is loaded on a DNA-cellulose column. The pooled material from the column is dialyzed and analyzed by gel filtration to have a molecular weight of about 63,000 daltons and by sucrose gradient centrifugation of about 68,000 daltons.

The use of thermostable enzymes, such as those prepared by Chien et al. and Kaledin et al., to amplify existing nucleic acid sequences in amounts that are large compared to the amount initially present was described U.S. Pat. Nos. 4,683, 195 and 4,683,202, which describe the PCR process, both disclosures of which are incorporated herein by reference. Primers, template, nucleotide triphosphates, the appropriate buffer and reaction conditions, and polymerase are used in the PCR process, which involves denaturation of target DNA, hybridization of primers, and synthesis of complementary strands. The extension product of each primer becomes a template for the production of the desired nucleic acid sequence. The two patents disclose that, if the polymerase employed is a thermostable enzyme, then polymerase need not be added after every denaturation step, because heat will not destroy the polymerase activity.

U.S. Pat. No. 4,889,818, European Patent Publication No. 258,017, and PCT Publication No. 89/06691, the disclosures of which are incorporated herein by reference, all describe the isolation and recombinant expression of an ~94 kDa thermostable DNA polymerase from Thermus aquaticus and the use of that polymerase in PCR. Although T. aquaticus DNA polymerase is especially preferred for use in PCR and other recombinant DNA techniques, there remains a need for other thermostable polymerases.

Accordingly, there is a desire in the art to produce a purified, thermostable DNA polymerase that may be used to improve the PCR process described above and to improve the results obtained when using a thermostable DNA polymerase in other recombinant techniques such as DNA sequencing, nick-translation, and even reverse transcription. The present invention helps meet that need by providing recombinant expression vectors and purification protocols for a DNA polymerase from Thermus species Z05.

SUMMARY OF THE INVENTION

Accordingly, the present invention provides a purified thermostable enzyme that catalyzes combination of nucleoside triphosphates to form a nucleic acid strand complementary to a nucleic acid template strand. The purified enzyme is the DNA polymerase activity from Thermus species Z05 (TZ05). This purified material may be used in a temperature-cycling amplification reaction wherein nucleic acid sequences are produced from a given nucleic acid sequence in amounts that are large compared to the amount initially present so that the sequences can be manipulated and/or analyzed easily.

The gene encoding TZ05 DNA polymerase enzyme from Thermus species Z05 has also been identified and cloned and provides yet another means to prepare the thermostable enzyme of the present invention. In addition to the portions of the gene encoding the TZ05 enzyme, derivatives of these gene portions encoding TZ05 DNA polymerase activity are also provided.

The invention also encompasses a stable enzyme composition comprising a purified, thermostable TZ05 enzyme as described above in a buffer containing one or more non-ionic polymeric detergents.

Finally, the invention provides a method of purification for the thermostable polymerase of the invention. This method involves preparing a crude extract from Thermus species Z05 or recombinant host cells, adjusting the ionic strength of the crude extract so that the DNA polymerase dissociates from nucleic acid in the extract, subjecting the extract to hydrophobic interaction chromatography, subjecting the extract to DNA binding protein affinity chromatography, and subjecting the extract to cation or anion or hydroxyapatite chromatography. In a preferred embodiment, these steps are performed sequentially in the order given above. The nucleotide binding protein affinity chromatography step is preferred for separating the DNA polymerase from endonuclease proteins.

DETAILED DESCRIPTION OF THE INVENTION

The present invention provides DNA sequences and expression vectors that encode TZ05 DNA polymerase. To facilitate understanding of the invention, a number of terms are defined below.

The terms "cell", "cell line", and "cell culture" can be used interchangeably and all such designations include progeny. Thus, the words "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "control sequences" refers to DNA sequences necessary for the expression of an operably linked coding sequence in a particular host organism. The control sequences that are suitable for procaryotes, for example, include a promoter, optionally an operator sequence, a ribosome binding site, and possibly other sequences. Eucaryotic cells am known to utilize promoters, polyadenylation signals, and enhancers.

The term "expression system" refers to DNA sequences containing a desired coding sequence and control sequences in operable linkage, so that hosts transformed with these sequences are capable of producing the encoded proteins. To effect transformation, the expression system may be included on a vector; however, the relevant DNA may also be integrated into the host chromosome.

The term "gene" refers to a DNA sequence that comprises control and coding sequences necessary for the production of a recoverable bioactive polypeptide or precursor. The polypeptide can be encoded by a full length coding sequence or by any portion of the coding sequence so long as the enzymatic activity is retained.

The term "operably linked" refers to the positioning of the coding sequence such that control sequences will function to drive expression of the protein encoded by the coding sequence. Thus, a coding sequence "operably linked" to control sequences refers to a configuration wherein the coding sequences can be expressed under the direction of a control sequence.

The term "mixture" as it relates to mixtures containing TZ05 polymerase refers to a collection of materials which includes TZ05 polymerase but which can also include other proteins. If the TZ05 polymerase is derived from recombinant host cells, the other proteins will ordinarily be those associated with the host. Where the host is bacterial, the contaminating proteins will, of course, be bacterial proteins.

The term "non-ionic polymeric detergents" refers to surface-active agents that have no ionic charge and that are characterized for purposes of this invention, by an ability to stabilize the TZ05 enzyme at a pH range of from about 3.5 to about 9.5, preferably from 4 to 8.5.

The term "oligonucleotide" as used herein is defined as a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be derived synthetically or by cloning.

The term "primer" as used herein refers to an oligonucleotide which is capable of acting as a point of initiation of synthesis when placed under conditions in which primer extension is initiated. An oligonucleotide "primer" may occur naturally, as in a purified restriction digest or be produced synthetically. Synthesis of a primer extension product which is complementary to a nucleic acid strand is initiated in the presence of four different nucleoside triphosphates and the TZ05 thermostable enzyme in an appropriate buffer at a suitable temperature. A "buffer" includes cofactors (such as divalent metal ions) and salt (to provide the appropriate ionic strength), adjusted to the desired pH. For TZ05 polymerase, the buffer preferably contains 1 to 3 mM of a magnesium salt, preferably $MgCl_2$, 50 to 200 µM of each nucleotide, and 0.2 to 1 µM of each primer, along with 50 mM KCl, 10 mM Tris buffer (pH 8.0–8.4), and 100 µg/ml gelatin (although gelatin is not required, and should be avoided in some applications, such as DNA sequencing).

A primer is single-stranded for maximum efficiency in amplification, but may alternatively be double-stranded. If double-stranded, the primer is first treated to separate its strands before being used to prepare extension products. The primer is usually an oligodeoxyribonucleotide. The primer must be sufficiently long to prime the synthesis of extension products in the presence of the polymerase enzyme. The exact length of a primer will depend on many factors, such as source of primer and result desired, and the reaction temperature must be adjusted depending on primer length and nucleotide sequence to ensure proper annealing of primer to template. Depending on the complexity of the target sequence, an oligonucleotide primer typically contains 15 to 35 nucleotides. Short primer molecules generally require lower temperatures to form sufficiently stable complexes with template.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

The terms "restriction endonucleases" and "restriction enzymes" refer to bacterial enzymes which cut double-stranded DNA at or near a specific nucleotide sequence.

The term "thermostable enzyme" refers to an enzyme which is stable to heat and is heat resistant and catalyzes (facilitates) combination of the nucleotides in the proper manner to form primer extension products that are complementary to a template nucleic acid strand. Generally, synthesis of a primer extension product begins at the 3' end of the primer and proceeds in the 5' direction along the template strand, until synthesis terminates.

The TZ05 thermostable enzyme of the present invention satisfies the requirements for effective use in the amplification reaction known as the polymerase chain reaction or PCR. The TZ05 enzyme does not become irreversibly denatured (inactivated) when subjected to the elevated temperatures for the time necessary to effect denaturation of double-stranded nucleic acids, a key step in the PCR process. Irreversible denaturation for purposes herein refers to permanent and complete loss of enzymatic activity. The heating conditions necessary for nucleic acid denaturation will depend, e.g., on the buffer salt concentration and the composition and length of the nucleic acids being denatured, but typically range from about 90° to about 105° C. for a time depending mainly on the temperature and the nucleic acid length, typically from a few seconds up to four minutes. Higher temperatures may be required as the buffer salt concentration and/or GC composition of the nucleic acid is increased. The TZ05 enzyme does not become irreversibly denatured for relatively short exposures to temperatures of about 90°–100° C.

The TZ05 thermostable enzyme has an optimum temperature at which it functions that is higher than about 45° C. Temperatures below 45° C. facilitate hybridization of primer to template, but depending on salt composition and concentration and primer composition and length, hybridization of primer to template can occur at higher temperatures (e.g., 45°–70° C.), which may promote specificity of the primer hybridization reaction. The TZ05 enzyme exhibits activity over a broad temperature range from about 37° C. to 90° C.

The present invention provides DNA sequences encoding the thermostable DNA polymerase activity of Thermus species Z05. The coding sequence has homology to portions of the DNA sequences encoding the thermostable DNA polymerases of *Thermosipho africanus* (Taf), *Thermotoga maritima* (Tma), *T. aquaticus* (Taq) strain YT1, *T. thermophilus* (Tth), and T. species sps17 (Tsps17). The entire TZ05 coding sequence and the deduced amino acid sequence is depicted below. For convenience, the amino acid sequence of this TZ05 polymerase is numbered for reference. Portions of the 5' and 3' noncoding regions of the T. species Z05 DNA polymerase gene are also shown.

```
  1 AAGCTTGGGCAGGCGCGGGCCTACGATGCCTTCTACGTGGCCCTG

46 GCCGAGAAGAAGAGGGCCCTCCTTTGGACGGCCGATGCCCGTTTG

91 GTCCAAGGTCTAAGGGCGTTGGGCTTCCCCGGGGTCAAGGGTTTA

136 GAGGAAGCATGAGCCTCACCCTGGCGGACAAAGTGGTCTACGAGG

181 AGGAGATCCAGAAAAGCCGCTTCATCGCCAAGGCGGCCCCCGTGG

226 CCTCGGAGGAGGAGGCCTTGGCGTTTTTGGCCGAGAACCGGGAGC

271 CTGAGGCCACCCACAACTGCTACGCCTACAAGATCGGCCTCCTCT

316 ACCGCTTCTCTGACGACGGGGAGCCTTCGGGCACCGCGGGCAGGC

361 CCATCCTCCACGCCATAGAGGCCCAGGGCCTGGACCGGGTGGCGG

406 TTCTGGTGGTGCGCTACTTCGGCGGGGTGAAGCTCGGGGCCGGAG

451 GGCTCGTGCGGGCCTATGGAGGGGTGGCGGCGGAGGCCCTAAGGC

496 AGGCGCCCAAGGTTCCCTTGGTGGAGCGGGTGGCGCTTGCCTTCC

541 TCGTGCCCTTCGCCGAGGTGGGCCGGGTCTACGCCCTCCTGGAGG

586 CCCGCGCCCTAAAGGCGGAGGAGACCTACACCCCGGAGGGCGTGC

631 GCTTCGCCCTCAGGCTTCCTGAGCCCGAGCGGGAAGGCTTCCTCC

676 AGGCGCTCCTGGACGCCACCCGGGGCCAGGTAGCCCTGGAGTAGC

721 ATGAAGGCGATGCTTCCGCTCTTTGAACCCAAAGGCCGGGTTCTC
  1 Met Lys Ala Met Leu Pro Leu Phe Glu Pro Lys Gly Arg Val Leu

766 CTGGTGGACGGCCACCACCTGGCCTACCGCACCTTCTTCGCCCTA
 16 Leu Val Asp Gly His His Leu Ala Tyr Arg Thr Phe Phe Ala Leu

811 AAGGGCCTCACCACGAGCCGGGGCGAACCGGTGCAGGCGGTTTAC
 31 Lys Gly Leu Thr Thr Ser Arg Gly Glu Pro Val Gln Ala Val Tyr

856 GGCTTCGCCAAGAGCCTCCTCAAGGCCCTGAAGGAGGACGGGTAC
 46 Gly Phe Ala Lys Ser Leu Leu Lys Ala Leu Lys Glu Asp Gly Tyr

901 AAGGCCGTCTTCGTGGTCTTTGACGCCAAGGCCCCTTCCTTCCGC
 61 Lys Ala Val Phe Val Val Phe Asp Ala Lys Ala Pro Ser Phe Arg

946 CACGAGGCCTACGAGGCCTACAAGGCAGGCCGCGCCCCGACCCCC
 76 His Glu Ala Tyr Glu Ala Tyr Lys Ala Gly Arg Ala Pro Thr Pro
```

-continued

```
 991 GAGGACTTCCCCCGGCAGCTCGCCCTCATCAAGGAGCTGGTGGAC
  91 Glu Asp Phe Pro Arg Gln Leu Ala Leu Ile  Lys Glu Leu Val Asp

1036 CTCCTGGGGTTTACTCGCCTCGAGGTTCCGGGCTTTGAGGCGGAG
 106 Leu Leu Gly Phe Thr Arg Leu Glu Val Pro Gly Phe Glu Ala Asp

1081 GACGTCCTCGCCACCCTGGCCAAGAAGGCGGAAAGGGAGGGGTAC
 121 Asp Val Leu Ala Thr Leu Ala Lys Lys Ala Glu Arg Glu Gly Tyr

1126 GAGGTGCGCATCCTCACCGCCGACCGGGACCTTTACCAGCTCGTC
 136 Glu Val Arg Ile  Leu Thr Ala Asp Arg Asp Leu Tyr Gln Leu Val

1171 TCCGACCGCGTCGCCGTCCTCCACCCCGAGGGCCACCTCATCACC
 151 Ser Asp Arg Val Ala Val Leu His  Pro Glu Gly His Leu Ile  Thr

1216 CCGGAGTGGCTTTGGGAGAAGTACGGCCTTAAGCCGGAGCAGTGG
 166 Pro Glu Trp Leu Trp Glu Lys Tyr Gly Leu Lys Pro Glu Gln Trp

1261 GTGGACTTCCGCGCCCTCGTGGGGGACCCCTCCGACAACCTCCCC
 181 Val Asp Phe Arg Ala Leu Val Gly Asp Pro Ser Asp Asn Leu Pro

1306 GGGGTCAAGGGCATCGGGGAGAAGACCGCCCTCAAGCTCCTCAAG
 196 Gly Val Lys Gly Ile  Gly Glu Lys Thr Ala Leu Lys Leu Leu Lys

1351 GAGTGGGGAAGCCTGGAAAATATCCTCAAGAACCTGGACCGGGTG
 211 Glu Trp Gly Ser Leu Glu Asn Ile  Leu Lys Asn Leu Asp Arg Val

1396 AAGCCGGAAAGCGTCCGGGAAAGGATCAAGGCCCACCTGGAAGAC
 226 Lys Pro Glu Ser Val Arg Glu Arg Ile  Lys Ala His Leu Glu Asp

1441 CTTAAGCTCTCCTTGGAGCTTTCCCGGGTGCGCTCGGACCTCCCC
 241 Leu Lys Leu Ser Leu Glu Leu Ser Arg Val Arg Ser Asp Leu Pro

1486 CTGGAGGTGGACTTCGCCCGGAGGCGGGAGCCTGACCGGGAAGGG
 256 Leu Glu Val Asp Phe Ala Arg Arg Arg Glu Pro Asp Arg Glu Gly

1531 CTTCGGGCCTTTTTGGAGCGCTTGGAGTTCGGCAGCCTCCTCCAC
 271 Leu Arg Ala Phe Leu Glu Arg Leu Glu Phe Gly Ser Leu Leu His

1576 GAGTTCGGCCTCCTCGAGGCCCCCGCCCCCCTGGAGGAGGCCCCC
 286 Glu Phe Gly Leu Leu Glu Ala Pro  Ala Pro  Leu Glu Glu Ala Pro

1621 TGGCCCCCGCCGGAAGGGGCCTTCGTGGGCTTCGTCCTCTCCCGC
 301 Trp Pro Pro Pro Glu Gly Ala Phe Val Gly Phe Val Leu Ser Arg

1666 CCCGAGCCCATGTGGGCGGAGCTTAAAGCCCTGGCCGCCTGCAAG
 316 Pro Glu Pro Met Trp Ala Glu Leu Lys Ala Leu Ala Ala Cys Lys

1711 GAGGGCCGGGTGCACCGGGCAAAGGACCCCTTGGCGGGGCTAAAG
 331 Glu Gly Arg Val His  Arg Ala Lys Asp Pro Leu Ala Gly Leu Lys

1756 GACCTCAAGGAGGTCCGAGGCCTCCTCGCCAAGGACCTCGCCGTT
 346 Asp Leu Lys Glu Val Arg Gly Leu Leu Ala Lys Asp Leu Ala Val

1801 TTGGCCCTTCGCGAGGGGCTGGACCTCGCGCCTTCGGACGACCCC
 361 Leu Ala Leu Arg Glu Gly Leu Asp Leu Ala Pro  Ser Asp Asp Pro

1846 ATGCTCCTCGCCTACCTCCTGGACCCCTCCAACACCACCCCCGAG
 376 Met Leu Leu Ala Tyr Leu Leu Asp Pro Ser Asn Thr Thr Pro Glu

1891 GGGGTGGCCCGGCGCTACGGGGGGGAGTGGACGGAGGACGCCGCC
 391 Gly Val Ala Arg Arg Tyr Gly Gly Glu Trp Thr Glu Asp Ala Ala

1936 CACCGGGCCCTCCTCGCCGAGCGGCTCCAGCAAAACCTCTTGGAA
 406 His Arg Ala Leu Leu Ala Glu Arg Leu Gln Gln Asn Leu Leu Glu

1981 CGCCTCAAGGGAGAGGAAAAGCTCCTTTGGCTCTACCAAGAGGTG
 421 Arg Leu Lys Gly Glu Glu Lys Leu Leu Trp Leu Tyr Gln Glu Val

2026 GAAAAGCCCCTCTCCCGGGTCCTGGCCCACATGGAGGCCACCGGG
 436 Glu Lys Pro Leu Ser Arg Val Leu Ala His Met Glu Ala Thr Gly

2071 GTAAGGCTGGACGTGGCCTATCTAAAGGCCCTTTCCCTGGAGCTT
 451 Val Arg Leu Asp Val Ala Tyr Leu Lys Ala Leu Ser Leu Glu Leu

2116 GCGGAGGAGATTCGCCGCCTCGAGGAGGAGGTCTTCCGCCTGGCG
 466 Ala Glu Glu Ile  Arg Arg Leu Glu Glu Glu Val Phe Arg Leu Ala

2161 GGCCACCCCTTCAACCTGAACTCCCGTGACCAGCTAGAGCGGGTG
 481 Gly His Pro Phe Asn Leu Asn Ser Arg Asp Gln Leu Glu Arg Val

2206 CTCTTTGACGAGCTTAGGCTTCCCGCCCTGGGCAAGACGCAAAAG
 496 Leu Phe Asp Glu Leu Arg Leu Pro Ala Leu Gly Lys Thr Gln Lys
```

-continued

```
2251 ACGGGGAAGCGCTCCACCAGCGCCGCGGTGCTGGAGGCCCTCAGG
 511 Thr Gly Lys Arg Ser Thr Ser Ala Ala Val Leu Glu Ala Leu Arg

2296 GAGGCCCACCCCATCGTGGAGAAGATCCTCCAGCACCGGGAGCTC
 526 Glu Ala His Pro Ile Val Glu Lys Ile Leu Gln His Arg Glu Leu

2341 ACCAAGCTCAAGAACACCTACGTGGACCCCCTCCCGGGCCTCGTC
 541 Thr Lys Leu Lys Asn Thr Tyr Val Asp Pro Leu Pro Gly Leu Val

2386 CACCCGAGGACGGGCCGCCTCCACACCCGCTTCAACCAGACAGCC
 556 His Pro Arg Thr Gly Arg Leu His Thr Arg Phe Asn Gln Thr Ala

2431 ACGGCCACGGGAAGGCTCTCTAGCTCCGACCCCAACCTGCAGAAC
 571 Thr Ala Thr Gly Arg Leu Ser Ser Ser Asp Pro Asn Leu Gln Asn

2476 ATCCCCATCCGCACCCCCTTGGGCCAGAGGATCCGCCGGGCCTTC
 586 Ile Pro Ile Arg Thr Pro Leu Gly Gln Arg Ile Arg Arg Ala Phe

2521 GTGGCCGAGGCGGGATGGGCGTTGGTGGCCCTGGACTATAGCCAG
 601 Val Ala Glu Ala Gly Trp Ala Leu Val Ala Leu Asp Tyr Ser Gln

2566 ATAGAGCTCCGGGTCCTCGCCCACCTCTCCGGGGACGAGAACCTG
 616 Ile Glu Leu Arg Val Leu Ala His Leu Ser Gly Asp Glu Asn Leu

2611 ATCAGGGTCTTCCAGGAGGGGAAGGACATCCACACCCAGACCGCA
 631 Ile Arg Val Phe Gln Glu Gly Lys Asp Ile His Thr Gln Thr Ala

2656 AGCTGGATGTTCGGCGTCTCCCCGGAGGCCGTGGACCCCCTGATG
 646 Ser Trp Met Phe Gly Val Ser Pro Glu Ala Val Asp Pro Leu Met

2701 CGCCGGGCGGCCAAGACGGTGAACTTCGGCGTCCTCTACGGCATG
 661 Arg Arg Ala Ala Lys Thr Val Asn Phe Gly Val Leu Tyr Gly Met

2746 TCCGCCCATAGGCTCTCCCAGGAGCTTGCCATCCCCTACGAGGAG
 676 Ser Ala His Arg Leu Ser Gln Glu Leu Ala Ile Pro Tyr Glu Glu

2791 GCGGTGGCCTTTATAGAGCGCTACTTCCAAAGCTTCCCCAAGGTG
 691 Ala Val Ala Phe Ile Glu Arg Tyr Phe Gln Ser Phe Pro Lys Val

2836 CGGGCCTGGATAGAAAAGACCCTGGAGGAGGGGAGGAAGCGGGGC
 706 Arg Ala Trp Ile Glu Lys Thr Leu Glu Glu Gly Arg Lys Arg Gly

2881 TACGTGGAAACCCTCTTCGGAAGAAGGCGCTACGTGCCCGACCTC
 721 Tyr Val Glu Thr Leu Phe Gly Arg Arg Arg Tyr Val Pro Asp Leu

2926 AACGCCCGGGTGAAGAGCGTCAGGGAGGCCGCGGAGCGCATGGCC
 736 Asn Ala Arg Val Lys Ser Val Arg Glu Ala Ala Glu Arg Met Ala

2971 TTCAACATGCCCGTCCAGGGCACCGCCGCCGACCTCATGAAGCTC
 751 Phe Asn Met Pro Val Gln Gly Thr Ala Ala Asp Leu Met Lys Leu

3016 GCCATGGTGAAGCTCTTCCCCCACCTCCGGGAGATGGGGGCCCGC
 766 Ala Met Val Lys Leu Phe Pro His Leu Arg Glu Met Gly Ala Arg

3061 ATGCTCCTCCAGGTCCACGACGAGCTCCTCCTGGAGGCCCCCCAA
 781 Met Leu Leu Gln Val His Asp Glu Leu Leu Leu Glu Ala Pro Gln

3106 GCGCGGGCCGAGGAGGTGGCGGCTTTGGCCAAGGAGGCCATGGAG
 796 Ala Arg Ala Glu Glu Val Ala Ala Leu Ala Lys Glu Als Met Glu

3151 AAGGCCTATCCCCTCGCCGTGCCCCTGGAGGTGGAGGTGGGGATC
 811 Lys Ala Tyr Pro Leu Ala Val Pro Leu Glu Val Glu Val Gly Ile

3196 GGGGAGGACTGGCTTTCCGCCAAGGGCTGAGGAAGCCCTGGTATA
 826 Gly Glu Asp Trp Leu Ser Ala Lys Gly

3241 GTGGCCGCCATGAGGCGCTACTTCGGCACCGACGGGGTGCGGGGG

3286 GAGGCGGGGAAGCCTCCTCTTACCCCGGAGTTTGTCCTAAAGCTC

3331 GGCCAGGCGGCGGGGGCCTATTTCCGGACCCAGGAAAAAAGGCCC

3376 GTGGTCCTCCTCGCCAAGGACACCCGGGAGTCCTCGGACCTCCTG

3421 GAGGCCGCCCTGGCGGCGGGGCTTATGAGCCAGGGGGTGCGGGTG

3466 GAGCACCTCGGGGTCCTCCCCACCCCGGGGGTCGCCCACCTCACC
```

-continued

```
3511 AAGGCCCTCAAGGCCACGGCGGGGGCGGTGATCTCGGCGAGCCAC

3556 AACCCCTACCAGGACAACGGCATCAAGTTCTTCGGCCCCACGGGG

3601 GAGACGCTCCCCGACGAGGCCGAGGAGGAAATCGAGCGCCTTCTC

3646 CTAGAAGACCACCCCACCCGGGGCATCGGCACGGTGGGGGACTTC

3691 CGGGAGGCCGAAAGGATGTACCTGGACTTCCTCCTNGCCCACGCC

3736 CCGGACCTCACGGGGCTCAAGGTGGGCCTGGACCTCGCCCACGGG

3781 GCCACCTACCGGGTGGNCCCCAAGCTCTTCCAGAAGGCGGGGGCC

3826 GAGGTCATGGCCTTCTTCAACACCCCAGACGGCCGGAACATCAAC

3871 CGGGGCTGCGGCTCCACCCACCCCGAGNCCTTGAGCCGCTTCGTG

3916 GCGGAGCTCGGGCTGGACCTGGNCCTCGCCTTTGACGGGGACGGG

3961 GACCGGGTGCAGTTCATAGACCGCAAGGGGCGCCTCTTCCACGGG

4006 GACCACGTCCTCTACCTCNCCGCCTTGGCCTTTGGGGAGAAGGGC

4051 GTGGTGGGGACGGTGATGAGCAACAT
```

The above nucleotide sequence was identified by a "degenerate primer" method that has broad utility and is an important aspect of the present invention. In the degenerate primer method, DNA fragments of any thermostable polymerase coding sequence corresponding to conserved domains of known thermostable DNA polymerases can be identified.

The degenerate primer method was developed by comparing the amino acid sequences of DNA polymerase proteins from Taq, Tth, T7, and E. coli polymerase I in which various conserved regions were identified. Primers corresponding to these conserved regions were then designed. As a result of the present invention, TZ05 sequences can be used to design other degenerate primers, as can the coding sequences of the Thermus species sps17 DNA polymerase gene (see U.S. Ser. No. 07/590,213, filed herewith at even date and incorporated herein by reference) and the Thermotoga maritima DNA polymerase gene (see U.S. Ser. No. 567,244, filed Aug. 13, 1990, and incorporated herein by reference), and the Thermosipho africanus DNA polymerase gene (see Ser. No. 07/590,490, filed herewith at even date and incorporated herein by reference). The generic utility of the degenerate primer process is exemplified herein by specific reference to the method as applied to cloning the TZ05 gene.

To clone the TZ05 DNA polymerase gene, conserved amino acid sequences of DNA polymerase enzymes were converted to all of the possible codons which represent each of the amino acids. Due to the degenerate nature of the genetic code, a given amino acid may be represented by several different codons. Where more than one base can be present in a codon for a given amino acid, the sequence is said to be degenerate.

The primers were then synthesized as a pool of all of the possible DNA sequences that could code for a given amino acid sequence. The amount of degeneracy of a given primer pool can be determined by multiplying the number of possible nucleotides at each position.

The greater the number of individual unique primer DNA sequences within a primer pool, the greater the probability that one of the unique primer sequences will bind to regions of the target chromosomal DNA other than the one desired; hence, the lesser the specificity of the resulting amplification. To increase the specificity of the amplification using degenerate primers, the pools are synthesized as subsets such that the entire group of subsets includes all possible DNA sequences encoding the given amino acid sequence, but each individual subset only includes a portion: for example, one pool may contain either a G or C at a certain position while another pool contains either an A or T at the same position. As described herein, these subpools are designated with a DG number (where number=99 to 200).

Both forward primers (directed from the 5' region toward the 3' region of the gene, complementary to the noncoding strand) and reverse primers (directed from the 3' region of the gene toward the 5' region of the gene, complementary to the coding strand) were designed for most of the conserved regions to clone TZ05 polymerase. The primers were designed with restriction sites at the 5' ends of the primers to facilitate cloning. The forward primers contained a BglII restriction site (AGATCT), while the reverse primers contained an EcoRI restriction site (GAATTC). In addition, the primers contained 2 additional nucleotides at the 5' end to increase the efficiency of cutting at the restriction site.

Degenerate primers were then used in PCR processes to amplify chromosomal DNA from Thermus species Z05. The products of the PCR processes using a combination of forward and reverse primer pools in conjunction with a series of temperature profiles were compared. When specific products of similar size to the product generated using Taq chromosomal DNA were produced, the PCR fragments were gel purified, reamplified and cloned into the vector pBSM13+HindIII::BglII (a derivative of the Stratagene™ vector pBSM+ in which the HindIII site of pBSM+ was convened to a BglII site). The PCR fragments were cloned and sequenced; fragments were identified as potential thermostable DNA polymerase coding sequences if the fragments contained sequences that encode regions of amino acid homology to other known polymerase protein sequences, particularly those of Taq polymerase and Tth polymerase.

The portions of the TZ05 DNA polymerase gene were then identified in the chromosomal DNA of Thermus species Z05 by Southern blot analysis. The TZ05 chromosomal DNA was digested with a variety of enzymes and transferred to nitrocellulose filters. Probes labeled with $^{32}$P or biotin-dUTP were generated for various regions of the gene from the cloned PCR products. The probes were hybridized to the nitrocellulose-bound genomic DNA, allowing identification of the molecular weight of the chromosomal DNA fragment hybridizing to the probe. The use of probes covering the 5' and 3' regions of the gene ensures that the DNA fragment(s) contain most if not all of the structural gene for the polymerase. Restriction enzymes can be identified that can be used to produce fragments that contain the structural gene in a single DNA fragment or in several DNA fragments to facilitate cloning.

Once identified, chromosomal DNA encoding portions of the TZ05 DNA polymerase gene was cloned. Chromosomal DNA was digested with the identified restriction enzymes, and size fractionated. Fractions containing the desired size range were concentrated, desalted, and cloned into the pBSM13+HindIII::BglII cloning vector. Clones were identified by hybridization using labeled probes generated from the previous cloned PCR products. The cloned fragments were identified by restriction enzyme analysis and Southern blot analysis.

The DNA sequence and amino acid sequence shown above and the DNA compounds that encode those sequences can be used to design and construct recombinant DNA expression vectors to drive expression of TZ05 DNA polymerase activity in a wide variety of host cells. A DNA compound encoding all or part of the DNA sequence shown above can also be used as a probe to identify thermostable polymerase-encoding DNA from other organisms, and the amino acid sequence shown above can be used to design peptides for use as immunogens to prepare antibodies that can be used to identify and purify a thermostable polymerase.

Whether produced by recombinant vectors that encode the above amino acid sequence or by native Thermus species Z05 cells, however, TZ05 DNA polymerase will typically be purified prior to use in a recombinant DNA technique. The present invention provides such purification methodology.

For recovering the native protein, the cells are grown using any suitable technique. Typically, the Thermus species Z05 cells are grown in a medium of: sodium citrate, 1 mM; potassium phosphate, pH 7.9, 5 mM; ammonium chloride, 10 mM; magnesium sulfate, 0.2 mM; calcium chloride, 0.1 mM; sodium chloride, 1 g/l; yeast extract, 1 g/l; tryptone, 1 g/l; glucose, 2 g/l; ferrous sulfate, 0.01 mM.

After cell growth, the isolation and purification of the enzyme takes place in six stages, each of which is carried out at a temperature below room temperature, preferably about 0° to about 4° C., unless stated otherwise. In the first stage or step, the cells, if frozen, are thawed, disintegrated by ultrasound, suspended in a buffer at about pH 7.5, and centrifuged.

In the second stage, the supernatant is collected and then fractionated by adding a salt such as dry ammonium sulfate. The appropriate fraction (typically 45–75% of saturation) is collected, dissolved in a 0.2M potassium phosphate buffer preferably at pH 6.5, and dialyzed against the same buffer.

The third step removes nucleic acids and some protein. The fraction from the second stage is applied to a DEAE-cellulose column equilibrated with the same buffer as used above. Then the column is washed with the same buffer and the flow-through protein-containing fractions, determined by absorbance at 280 nm, are collected and dialyzed against a 10 mM potassium phosphate buffer, preferably with the same ingredients as the first buffer, but at a pH of 7.5.

In the fourth step, the fraction so collected is applied to a hydroxyapatite column equilibrated with the buffer used for dialysis in the third step. The column is then washed and the enzyme eluted with a linear gradient of a buffer such as 0.01M to 0.5M potassium phosphate buffer at pH 7.5 containing 10 mM 2-mercaptoethanol and 5% glycerine. The pooled fractions containing thermostable DNA polymerase activity are dialyzed against the same buffer used for dialysis in the third step.

In the fifth stage, the dialyzed fraction is applied to a DEAE-cellulose column, equilibrated with the buffer used for dialysis in the third step. The column is then washed and the enzyme eluted with a linear gradient of a buffer such as 0.01 to 0.6M KCl in the buffer used for dialysis in the third step. Fractions with thermostable enzyme activity are then tested for contaminating deoxyribonucleases (endo- and exonucleases) using any suitable procedure. For example, the endonuclease activity may be determined electrophoretically from the change in molecular weight of phage lambda DNA or supercoiled plasmid DNA after incubation with an excess of DNA polymerase. Similarly, exonuclease activity may be determined electrophoretically from the change in molecular weight of restriction enzyme-cleaved DNA after treatment with the DNA polymerase fraction. The fractions determined to have polymerase activity but no deoxyribonucleases activity are pooled and dialyzed against the same buffer used in the third step.

In the sixth step, the pooled fractions are placed on a phosphocellulose column with a set bed volume. The column is washed and the enzyme eluted with a linear gradient of a buffer such as 0.01 to 0.4M KCl in a potassium phosphate buffer at pH 7.5. The pooled fractions having thermostable polymerase activity and no deoxyribonuclease activity are dialyzed against a buffer at pH 8.0.

The molecular weight of the DNA polymerase purified from Thermus species Z05 may be determined by any technique, for example, by SDS-PAGE analysis using protein molecular weight markers. The purification protocol of native TZ05 DNA polymerase is described in detail in Example 1. Purification of the recombinant TZ05 polymerase of the invention can be carried out with similar methodology.

The entire coding sequence of the TZ05 DNA polymerase gene is not required, however, to produce a biologically active gene product with DNA polymerase activity. The availability of DNA encoding the TZ05 DNA polymerase sequence provides the opportunity to modify the coding sequence so as to generate mutein (mutant protein) forms also having DNA polymerase activity. The amino(N)-terminal portion of the TZ05 polymerase is not believed to be necessary for activity. Using recombinant DNA methodology, one can delete up to approximately one-third of the N-terminal coding sequence of the TZ05 gene, clone, and express a gene product that is quite active in polymerase assays. Because certain N-terminal shortened forms of the polymerase are active, the gene constructs used for expression of these polymerases can include the corresponding shortened forms of the coding sequence.

In addition to the N-terminal deletions, individual amino acid residues in the peptide chain of TZ05 polymerase may be modified by oxidation, reduction, or other derivation, and the protein may be cleaved to obtain fragments that retain activity. Such alterations that do not destroy activity do not remove the protein from the definition of a protein with TZ05 polymerase activity and so am specifically included within the scope of the present invention.

Modifications to the primary structure of the TZ05 gene DNA polymerase by deletion, addition, or alteration so as to change the amino acids incorporated into the TZ05 DNA polymerase during translation can be made without destroying the high temperature DNA polymerase activity of the protein. Such substitutions or other alterations result in the production of proteins having an amino acid sequence encoded by DNA falling within the contemplated scope of the present invention. Likewise, the cloned genomic sequence, or homologous synthetic sequences, of the TZ05 DNA polymerase gene can be used to express a fusion polypeptide with TZ05 DNA polymerase activity or to express a protein with an amino acid sequence identical to that of native TZ05 DNA polymerase. In addition, such expression can be directed by the TZ05 DNA polymerase gene control sequences or by a control sequence that functions in whatever host is chosen to express the TZ05 DNA polymerase.

Thus, the present invention provides a coding sequence for TZ05 DNA polymerase from which expression vectors applicable to a variety of host systems can be constructed and the coding sequence expressed. Portions of the TZ05 polymerase-encoding sequence are also useful as probes to retrieve other thermostable polymerase-encoding sequences in a variety of species. Accordingly, oligonucleotide probes that encode at least four to six amino acids can be synthesized and used to retrieve additional DNAs encoding a thermostable polymerase. Because there may not be an exact match between the nucleotide sequence of the thermostable DNA polymerase gene of Thermus species Z05 and the corresponding gene of other species, oligomers containing approximately 12-18 nucleotides (encoding the four to six amino sequence) are usually necessary to obtain hybridization under conditions of sufficient stringency to eliminate false positives. Sequences encoding six amino acids supply ample information for such probes.

The present invention, by providing coding sequences and amino acid sequences for TZ05 DNA polymerase, therefore enables the isolation of other thermostable polymerase enzymes and the coding sequences for those enzymes. The deduced amino acid sequence of the TZ05 DNA polymerase protein is very similar to the amino acid sequences for other thermostable DNA polymerases, such as those from Taq and Tth (see Ser. No. 455,967, filed Dec. 22, 1989, incorporated herein by reference).

However, regions of dissimilarity between the coding sequences of thermostable DNA polymerases can also be used as probes to identify other thermostable polymerase coding sequences which encode enzymes having some properties of one known thermostable polymerase and perhaps different properties. For example, the coding sequence for a thermostable polymerase having some properties of Taq and other divergent properties of TZ05 may be identified by using probes comprising regions of dissimilarity between Taq and TZ05.

Whether one desires to produce an enzyme identical to native TZ05 DNA polymerase or a derivative or homologue of that enzyme, the production of a recombinant form of TZ05 polymerase typically involves the construction of an expression vector, the transformation of a host cell with the vector, and culture of the transformed host cell under conditions such that expression will occur.

To construct the expression vector, a DNA is obtained that encodes the mature (used here to include all muteins) enzyme or a fusion of the TZ05 polymerase to an additional sequence that does not destroy activity or to an additional sequence cleavable under controlled conditions (such as treatment with peptidase) to give an active protein. The coding sequence is then placed in operable linkage with suitable control sequences in an expression vector. The vector can be designed to replicate autonomously in the host cell or to integrate into the chromosomal DNA of the host cell. The vector is used to transform a suitable host, and the transformed host is cultured under conditions suitable for expression of recombinant TZ05 polymerase. The TZ05 polymerase is isolated from the medium or from the cells, although recovery and purification of the protein may not be necessary in some instances.

Each of the foregoing steps can be done in a variety of ways. For example, the desired coding sequence may be obtained from genomic fragments and used directly in appropriate hosts. The construction of expression vectors operable in a variety of hosts is made using appropriate replicons and control sequences, as set forth generally below. Construction of suitable vectors containing the desired coding and control sequences employs standard ligation and restriction techniques that are well understood in the art. Isolated plasmids, DNA sequences, or synthesized oligonucleotides are cleaved, modified, and religated in the form desired. Suitable restriction sites can, if not normally available, be added to the ends of the coding sequence so as to facilitate construction of an expression vector, as exemplified below.

Site-specific DNA cleavage is performed by treating with the suitable restriction enzyme (or enzymes) under conditions that are generally understood in the art and specified by the manufacturers of commercially available restriction enzymes. See, e.g., New England Biolabs, Product Catalog. In general, about 1 μg of plasmid or other DNA is cleaved by one unit of enzyme in about 20 μl of buffer solution; in the examples below, an excess of restriction enzyme is generally used to ensure complete digestion of the DNA. Incubation times of about one to two hours at about 37° C. are typical, although variations can be tolerated. After each incubation, protein is removed by extraction with phenol and chloroform; this extraction can be followed by ether extraction and recovery of the DNA from aqueous fractions by precipitation with ethanol. If desired, size separation of the cleaved fragments may be performed by polyacrylamide gel or agerose gel electrophoresis using standard techniques. See, e.g., *Methods in Enzymology*, 1980, 65:499–560.

Restriction-cleaved fragments with single-strand "overhanging" termini can be made blunt-ended (double-strand ends) by treating with the large fragment of *E. coli*. DNA polymerase I (Klenow) in the presence of the four deoxynucleoside triphosphates (dNTPs) using incubation times of about 15 to 25 minutes at 20° C. to 25° C. in 50 mM Tris pH 7.6, 50 mM NaCl, 10 mM $MgCl_2$, 10 mM DTT, and 5 to 10 μM dNTPs. The Klenow fragment fills in at 5' protruding ends, but chews back protruding 3' single strands, even though the four dNTPs are present. If desired, selective repair can be performed by supplying only one of the, or selected, dNTPs within the limitations dictated by the nature of the protruding ends. After treatment with Klenow, the mixture is extracted with phenol/chloroform and ethanol precipitated. Similar results can be achieved using S1 nuclease, because treatment under appropriate conditions with S1 nuclease results in hydrolysis of any single-stranded portion of a nucleic acid.

Synthetic oligonucleotides can be prepared using the triester method of Matteucci et al., 1981, *J. Am. Chem. Soc.* 103:3185–3191, or automated synthesis methods. Kinasing of single strands prior to annealing or for labeling is achieved using an excess, e.g., approximately 10 units, of polynucleotide kinase to 0.5 μM substrate in the presence of 50 mM Tris, pH 7.6, 10 mM $MgCl_2$, 5 mM dithiothreitol (DTT), and 1 to 2 μM ATP. If kinasing is for labeling of probe, the ATP will be labeled with $^{32}P$.

Ligations are performed in 15–30 μl volumes under the following standard conditions and temperatures: 20 mM Tris-Cl, pH 7.5, 10 mM $MgCl_2$, 10 mM DTT, 33 μg/ml BSA, 10 mM–50 mM NaCl, and either 40 μM ATP and 0.01–0.02 (Weiss) units T4 DNA ligase at 20° C. (for ligation of fragments with complementary single-stranded ends) or 1 mM ATP and 0.3–0.6 units T4 DNA ligase at 14° C. (for "blunt end" ligation). Intermolecular ligations of fragments with complementary ends are usually performed at 33–100 μg/ml total DNA concentrations (5–100 nM total ends concentration). Intermolecular blunt end ligations (usually employing a 20–30 fold molar excess of linkers, optionally) are performed at 1 μM total ends concentration.

In vector construction, the vector fragment is commonly treated with bacterial or calf intestinal alkaline phosphatase (BAP or CIAP) to remove the 5' phosphate and prevent religation and reconstruction of the vector. BAP and CIAP digestion conditions are well known in the art, and published protocols usually accompany the commercially available BAP and CIAP enzymes. To recover the nucleic acid fragments, the preparation is extracted with phenol-chloroform and ethanol precipitated to remove AP and purify the DNA. Alternatively, religation of unwanted vector fragments can be prevented by restriction enzyme digestion before or after ligation, if appropriate restriction sites are available.

For portions of vectors or coding sequences that require sequence modifications, a variety of site-specific primer-directed mutagenesis methods are available. The polymerase chain reaction (PCR) can be used to perform site-specific mutagenesis. In another technique now standard in the art, a synthetic oligonucleotide encoding the desired mutation is used as a primer to direct synthesis of a complementary nucleic acid sequence of a single-stranded vector, such as pBS13+, that serves as a template for construction of the extension product of the mutagenizing primer. The mutagenized DNA is transformed into a host bacterium, and cultures of the transformed bacteria are plated and identified. The identification of modified vectors may involve transfer of the DNA of selected transformants to a nitrocellulose filter or other membrane and the "lifts" hybridized with kinased synthetic mutagenic primer at a temperature that permits hybridization of an exact match to the modified sequence but prevents hybridization with the original unmutagenized strand. Transformants that contain DNA that hybridizes with the probe are then cultured (the sequence of the DNA is generally confirmed by sequence analysis) and serve as a reservoir of the modified DNA.

In the construction set forth below, correct ligations for plasmid construction are confirmed by first transforming *E. coli* strain DG101 or another suitable host with the ligation mixture. Successful transformants are selected by ampicillin, tetracycline or other antibiotic resistance or sensitivity or by using other markers, depending on the mode of plasmid construction, as is understood in the art. Plasmids from the transformants are then prepared according to the method of Clewell et al., 1969, Proc. Natl. Acad. Sci. U.S.A. 62:1159, optionally following chloramphenicol amplification (Clewell, 1972, *J. Bacteriol.* 110:667). Another method for obtaining plasmid DNA is described as the "Base-Acid" extraction method at page 11 of the Bethesda Research Laboratories publication *Focus*, volume 5, number 2, and very pure plasmid DNA can be obtained by replacing steps 12 through 17 of the protocol with CsCl/ethidium bromide ultracentrifugation of the DNA. The isolated DNA is analyzed by restriction enzyme digestion and/or sequenced by the dideoxy method of Sanger et al., 1977, *Proc. Natl. Acad. Sci. U.S.A.* 74:5463, as further described by Messing et al., 1981, *Nuc. Acids Res.* 9:309, or by the method of Maxam et al., 1980, *Methods in Enzymology* 65:499.

The control sequences, expression vectors, and transformation methods are dependent on the type of host cell used to express the gene. Generally, procaryotic, yeast, insect, or mammalian cells are used as hosts. Procaryotic hosts are in general the most efficient and convenient for the production of recombinant proteins and are therefore preferred for the expression of TZ05 polymerase.

The procaryote most frequently used to express recombinant proteins is *E. coli*. For cloning and sequencing, and for expression of constructions under control of most bacterial promoters, *E. coli* K12 strain MM294, obtained from the *E. coli* Genetic Stock Center under GCSC #6135, can be used as the host. For expression vectors with the $P_LN_{RBS}$ control sequence, *E. coli* K12 strain MC1000 lambda lysogen, $N_7N_{53}I857$ $SusP_{80}$, ATCC 39531, may be used. *E. coli* DG116, which was deposited with the ATCC (ATCC 53606) on Apr. 7, 1987, and *E. coli* KB2, which was deposited with the ATCC (ATCC 53075) on Mar. 29, 1985, are also useful host cells. For M13 phage recombinants, *E. coli* strains susceptible to phage infection, such as *E. coli* K12 strain DG98, are employed. The DG98 strain was deposited with the ATCC (ATCC 39768) on Jul. 13, 1984.

However, microbial strains other than *E. coli* can also be used, such as bacilli, for example *Bacillus subtilis*, various species of Pseudomonas, and other bacterial strains, for recombinant expression of TZ05 DNA polymerase. In such procaryotic systems, plasmid vectors that contain replication sites and control sequences derived from the host or a species compatible with the host are typically used.

For example, *E. coli* is typically transformed using derivatives of pBR322, described by Bolivar et al., 1977, *Gene* 2:95. Plasmid pBR322 contains genes for ampicillin and tetracycline resistance. These drug resistance markers can be either retained or destroyed in constructing the desired vector and so help to detect the presence of a desired recombinant. Commonly used procaryotic control sequences, i.e., a promoter for transcription initiation, optionally with an operator, along with a ribosome binding site sequence, include the β-lactamase (penicillinase) and lactose (lac) promoter systems (Chang et al., 1977, *Nature* 198:1056), the tryptophan (trp) promoter system (Goeddel et al., 1980, *Nuc. Acids Res.* 8:4057), and the lambda-derived $P_L$ promoter (Shimatake et al., 1981, *Nature* 292:128) and N-gene ribosome binding site ($N_{RBS}$). A portable control system cassette is set forth in U.S. Pat. No. 4,711,845, issued Dec. 8, 1987. This cassette comprises a P$_L$ promoter operably linked to the N$_{RBS}$ in turn positioned upstream of a third DNA sequence having at least one restriction site that permits cleavage within six bp 3' of the N$_{RBS}$ sequence. Also useful is the phosphatase A (phoA) system described by Chang et al. in European Patent Publication No. 196,864, published Oct. 8, 1986. However, any available promoter system compatible with procaryotes can be used to construct a TZ05 expression vector of the invention.

In addition to bacteria, eucaryotic microbes, such as yeast, can also be used as recombinant host cells. Laboratory strains of *Saccharomyces cerevisiae*, Baker's yeast, are most often used, although a number of other strains are commonly available. While vectors employing the two micron origin of replication are common (Broach, 1983, *Meth. Enz.* 101:307), other plasmid vectors suitable for yeast expression are known (see, for example, Stinchcomb et al., 1979, *Nature* 282:39; Tschempe et al., 1980, *Gene* 10:157; and Clarke et al., 1983, *Meth. Enz.* 101:300). Control sequences for yeast vectors include promoters for the synthesis of glycolytic enzymes (Hess et al., 1968, *J. Adv. Enzyme. Reg.* 7: 149; Holland et al., 1978, *Biotechnology* 17:4900; and Holland et al., 1981, *J. Biol. Chem.* 256:1385). Additional promoters known in the art include the promoter for 3-phosphoglycerate kinase (Hitzeman et al., 1980, *J. Biol. Chem.* 255:2073) and those for other glycolytic enzymes, such as glyceraldehyde 3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters that have the additional advantage of transcription controlled by growth conditions are the promote, regions for alcohol dehydrogenase 2, isocytochrome C, acid phosphatase, degradative enzymes associated with nitrogen metabolism, and enzymes responsible for reallose and galaclose utilization (Holland, supra).

Terminator sequences may also be used to enhance expression when placed at the 3' end of the coding sequence. Such terminators are found in the 3' untranslated region following the coding sequences in yeast-derived genes. Any vector containing a yeast-compatible promoter, origin of replication, and other control sequences is suitable for use in constructing yeast TZ05 expression vectors.

The TZ05 gene can also be expressed in eucaryotic host cell cultures derived from multicellular organisms. See, for example, *Tissue Culture*, Academic Press, Cruz and Patterson, editors (1973). Useful host cell lines include COS-7, COS-A2, CV-1, murine cells such as murine myelomas N51 and VERO, HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers et al., 1978, *Nature* 273:113), or other viral promoters such as those derived from polyoma, adenovirus 2, bovine papilloma virus (BPV), or arian sarcoma viruses, or immunoglobulin promoters and heat shock promoters. A system for expressing DNA in mmnmalian systems using a BPV vector system is disclosed in U.S. Pat. No. 4,419,446. A modification of this system is described in U.S. Pat. No. 4,601,978. General aspects of mammalian cell host system transformations have been described by Axel, U.S. Pat. No. 4,399,216. "Enhancer" regions are also important in optimizing expression; these are, generally, sequences found upstream of the promoter region. Origins of replication may be obtained, if needed, from viral sources. However, integration into the chromosome is a common mechanism for DNA replication in eucaryotes.

Plant cells can also be used as hosts, and control sequences compatible with plant cells, such as the nopaline synthase promoter and polyadenylation signal sequences (Depicker et al., 1982, *J. Mol. Appl. Gen.* 1:561) are available. Expression systems employing insect cells utilizing the control systems provided by baculovirus vectors have also been described (Miller et al., in *Genetic Engineering* (1986). Setlow et al., eds., Plenum Publishing, Vol. 8, pp. 277–297). Insect cell-based expression can be accomplished in *Spodoptera frugipeida*. These systems are also successful in producing recombinant TZ05 polymerase.

Depending on the host cell used, transformation is done using standard techniques appropriate to such cells. The calcium treatment employing calcium chloride, as described by Cohen, 1972, *Proc. Natl. Acad. Sci. U.S.A.* 69:2110 is used for procaryotes or other cells that contain substantial cell wall barriers. Infection with *Agrobacterium tumefaciens* (Shaw et al., 1983, *Gene* 23:315) is used for certain plant cells. For mammalian cells, the calcium phosphate precipitation method of Graham and van der Eb, 1978, *Virology* 52:546 is preferred. Transformations into yeast are carried out according to the method of Van Solingen et al., 1977, *J. Bact.* 130:946, and Hsiao et al., 1979, *Proc. Natl. Acad. Sci. U.S.A.* 76:3829.

Once the TZ05 DNA polymerase has been expressed in a recombinant host cell, purification of the protein may be desired. Although a variety of purification procedures can be used to purify the recombinant thermostable polymerase of the invention, fewer steps may be necessary to yield an enzyme preparation of equal purity. Because *E. coli* host proteins are heat-sensitive, the recombinant thermostable TZ05 DNA polymerase can be substantially enriched by heat inactivating the crude lysate. This step is done in the presence of a sufficient amount of salt (typically 0.3M ammonium sulfate) to ensure dissociation of the TZ05 DNA polymerase from the host DNA and to reduce ionic interactions of TZ05 DNA polymerase with other cell lysate proteins.

In addition, the presence of 0.3M ammonium sulfate promotes hydrophobic interaction with a phenyl sepharose column. Hydrophobic interaction chromatography is a separation technique in which substances are separated on the basis of differing strengths of hydrophobic interaction with an uncharged bed material containing hydrophobic groups. Typically, the column is first equilibrated under conditions favorable to hydrophobic binding, such as high ionic strength. A descending salt gradient may then be used to elute the sample.

According to the invention, an aqueous mixture (containing either native or recombinant TZ05 DNA polymerase) is loaded onto a column containing a relatively strong hydrophobic gel such as phenyl sepharose (manufactured by Pharmacia) or Phenyl TSK (manufactured by Toyo Soda). To promote hydrophobic interaction with a phenyl sepharose column, a solvent is used which contains, for example, greater than or equal to 0.3M ammonium sulfate. The column and the sample are adjusted to 0.3M ammonium sulfate in 50 mM Tris (pH 7.5) and 0.5 mM EDTA ("TE") buffer that also contains 0.5 mM DTT, and the sample is applied to the column. The column is washed with the 0.3M ammonium sulfate buffer. The enzyme may then be eluted with solvents which attenuate hydrophobic interactions, such as decreasing salt gradients, or increasing gradients or addition of ethylene or propylene glycol, or urea. For native TZ05 DNA polymerase, a preferred embodiment involves washing the column with 2M urea in 20% ethylene glycol in TE-DTT wash.

For long-term stability, TZ05 DNA polymerase enzyme can be stored in a buffer that contains one or more non-ionic polymeric detergents. Such detergents are generally those that have a molecular weight in the range of approximately 100 to 250,000 daltons, preferably about 4,000 to 200,000 daltons and stabilize the enzyme at a pH of from about 3.5 to about 9.5, preferably from about 4 to 8.5. Examples of such detergents include those specified on pages 295-298 of McCutcheon's *Emulsifiers & Detergents*, North American edition (1983), published by the McCutcheon Division of MC Publishing Co., 175 Rock Road, Glen Rock, N.J. (U.S.A.).

Preferably, the detergents are selected from the group comprising ethoxylated fatty alcohol ethers and lauryl ethers, ethoxylated alkyl phenols, octylphenoxy polyethoxy ethanol compounds, modified oxyethylated and/or oxypropylated straight-chain alcohols, polyethylene glycol monooleate compounds, polysorbate compounds, and phenolic fatty alcohol ethers. More particularly preferred are Tween 20, a polyoxyethylated (20) sorbitan monolaurate from ICI Americas Inc., Wilmington, Del., and Iconol NP-40, an ethoxylated alkyl phenol (nonyl) from BASF Wyandotte Corp. Parsippany, N.J.

The thermostable enzyme of this invention may be used for any purpose in which such enzyme activity is necessary or desired. In a particularly preferred embodiment, the enzyme catalyzes the nucleic acid amplification reaction known as PCR. This process for amplifying nucleic acid sequences is disclosed and claimed in U.S. Pat. No. 4,683, 202, issued Jul. 28, 1987, the disclosure of which is incorporated herein by reference. The PCR nucleic acid amplification method involves amplifying at least one specific nucleic acid sequence contained in a nucleic acid or a mixture of nucleic acids and in the most common embodiment, produces double-stranded DNA.

For ease of discussion, the protocol set forth below assumes that the specific sequence to be amplified is contained in a double-stranded nucleic acid. However, the process is equally useful in amplifying single-stranded nucleic acid, such as mRNA, although in the preferred embodiment the ultimate product is still double-stranded DNA. In the amplification of a single-stranded nucleic acid, the first step involves the synthesis of a complementary strand (one of the two amplification primers can be used for this purpose), and the succeeding steps proceed as in the double-stranded amplification process described below.

This amplification process comprises the steps of:

(a) contacting each nucleic acid strand with four different nucleoside triphosphates and one oligonucleotide primer for each strand of the specific sequence being amplified, wherein each primer is selected to be substantially complementary to the different strands of the specific sequence, such that the extension product synthesized from one primer, when it is separated from its complement, can serve as a template for synthesis of the extension product of the other primer, said contacting being at a temperature which allows hybridization of each primer to a complementary nucleic acid strand;

(b) contacting each nucleic acid strand; at the same time as or after step (a), with a DNA polymerase from Thermus species Z05 which enables combination of the nucleoside triphosphates to form primer extension products complementary to each strand of the specific nucleic acid sequence;

(c) maintaining the mixture from step (b) at an effective temperature for an effective time to promote the activity of the enzyme and to synthesize, for each different sequence being amplified, an extension product of each primer which is complementary to each nucleic acid strand template, but not so high as to separate each extension product from the complementary strand template;

(d) heating the mixture from step (c) for an effective time and at an effective temperature to separate the primer extension products from the templates on which they were synthesized to produce single-stranded molecules but not so high as to denature irreversibly the enzyme;

(e) cooling the mixture from step (d) for an effective time and to an effective temperature to promote hybridization of a primer to each of the single-stranded molecules produced in step (d); and (f) maintaining the mixture from step (e) at an effective temperature for an effective time to promote the activity of the enzyme and to synthesize, for each different sequence being amplified, an extension product of each primer which is complementary to each nucleic acid template produced in step (d) but not so high as to separate each extension product from the complementary strand template. The effective times and temperatures in steps (e) and (f) may coincide, so that steps (e) and (f) can be carried out simultaneously. Steps (d)-(f) are repeated until the desired level of amplification is obtained.

The amplification method is useful not only for producing large amounts of a specific nucleic acid sequence of known sequence but also for producing nucleic acid sequences which are known to exist but are not completely specified. One need know only a sufficient number of bases at both ends of the sequence in sufficient detail so that two oligonucleotide primers can be prepared which will hybridize to different strands of the desired sequence at relative positions along the sequence such that an extension product synthesized from one primer, when separated from the template (complement), can serve as a template for extension of the other primer. The greater the knowledge about the bases at both ends of the sequence, the greater can be the specificity of the primers for the target nucleic acid sequence.

In any case, an initial copy of the sequence to be amplified must be available, although the sequence need not be pure or a discrete molecule. In general, the amplification process involves a chain reaction for producing at least one specific nucleic acid sequence, called the "target" sequence, given that (a) the ends of the target sequence are known in sufficient detail that oligonucleotides can be synthesized which will hybridize to them, and (b) a small amount of the sequence is available to initiate the chain reaction. The product accumulates exponentially relative to the number of reaction steps involved. The product of the chain reaction is a discrete nucleic acid duplex with termini corresponding to the ends of the specific primers employed.

Any nucleic acid sequence, in purified or nonpurified form, can be utilized as the starting nucleic acid(s), provided it contains or is suspected to contain the specific nucleic acid sequence desired. The nucleic acid to be amplified can be obtained from any source, for example, from plasmids such as pBR322, from cloned DNA or RNA, from natural DNA or RNA from any source, including bacteria, yeast, viruses, organelles, and higher organisms such as plants and animals, or from preparations of nucleic acid made in vitro. DNA or RNA may be extracted from blood, tissue material such as chorionic villi, or amniotic cells by a variety of techniques. See, e.g., Maniatis et al., supra, pp. 280-281. Thus, the process may employ, for example, DNA or RNA, including messenger RNA, which DNA or RNA may be single-stranded or double-stranded. In addition, a DNA-RNA hybrid which contains one strand of each may be utilized. A mixture of any of these nucleic acids can also be employed as can nucleic acids produced from a previous amplification reaction (using the same or different primers). The specific nucleic acid sequence to be amplified may be only a fraction of a large molecule or can be present initially as a discrete molecule, so that the specific sequence constitutes the entire nucleic acid.

The sequence to be amplified need not be present initially in a pure form; the sequence can be a minor fraction of a complex mixture, such as a portion of the β-globin gene contained in whole human DNA (as exemplified in Saiki et al., 1985, *Science* 230:1530–1534) or a portion of a nucleic acid sequence due to a particular microorganism, which organism might constitute only a very minor fraction of a particular biological sample. The cells can be directly used in the amplification process after suspension in hypotonic buffer and heat treatment at about 90°–100° C. until cell lysis and dispersion of intracellular components occur (generally 1 to 15 minutes). After the heating step, the amplification reagents may be added directly to the lysed cells. The starting nucleic acid sequence may contain more than one desired specific nucleic acid sequence. The amplification process is useful not only for producing large amounts of one specific nucleic acid sequence but also for amplifying simultaneously more than one different specific nucleic acid sequence located on the same or different nucleic acid molecules.

Primers play a key role in the PCR process. The word "primer" as used in describing the amplification process can refer to more than one primer, particularly in the case where there is some ambiguity in the information regarding the terminal sequence(s) of the fragment to be amplified. For instance, in the case where a nucleic acid sequence is inferred from protein sequence information, a collection of primers containing sequences rapresenting all possible codon variations based on degeneracy of the genetic code will be used for each strand. One primer from this collection will be sufficiently homologous with the end of the desired sequence to be amplified to be useful for amplification.

In addition, more than one specific nucleic acid sequence can be amplified from the first nucleic acid or mixture of nucleic acids, so long as the appropriate number of different oligonucleotide primers are utilized. For example, if two different specific nucleic acid sequences axe to be produced, four primers are utilized. Two of the primers are specific for one of the specific nucleic acid sequences and the other two primers are specific for the second specific nucleic acid sequence. In this manner, each of the two different specific sequences can be produced exponentially by the present process. When allelic variants or different members of a multigene family are to be amplified, however, one can often amplify several different sequences with a single set of primers.

A sequence within a given sequence can be amplified after a given number of amplifications to obtain greater specificity of the reaction by adding after at least one cycle of amplification a set of primers that are complementary to internal sequences (that are not on the ends) of the sequence to be amplified. Such primers may be added at any stage and will provide a shorter amplified fragment. Alternately, a longer fragment can be prepared by using primers with non-complementary 5' ends but having some 3' overlap with the 5' ends of the primers previously utilized in the amplification.

Primers also play a key role when the amplification process is used for in vitro mutagenesis. The product of an amplification reaction where the primers employed are not exactly complementary to the original template will contain the sequence of the primer rather than the template, so introducing an in vitro mutation. Although the initial cycles may be somewhat inefficient, due to the mismatch between the mutagenic primer and the target, in further cycles the mutation will be amplified with an undiminished efficiency because no further mispaired priming is required. The process of making an altered DNA sequence as described above could be repeated on the altered DNA using different primers to induce further sequence changes. In this way, a series of mutated sequences can gradually be produced wherein each new addition to the series differs from the last in a minor way, but from the original DNA soume sequence in an increasingly major way.

Because the primer can contain as part of its sequence a non-complementary sequence, provided that a sufficient amount of the primer contains a sequence that is complementary to the strand to be amplified, many other advantages can be realized. For example, a nucleotide sequence that is not complementary to the template sequence (such as, e.g., a promoter, linker, coding sequence, etc.) may be attached at the 5' end of one or both of the primers and so appended to the product of the amplification process. After the extension primer is added, sufficient cycles are run to achieve the desired amount of new template containing the non-complementary nucleotide insert. This allows production of large quantifies of the combined fragments in a relatively short period of time (e.g., two hours or less) using a simple technique.

Oligonucleotide primers can be prepared using any suitable method, such as, for example, the phosphodiester and phosphodiester methods described above, or automated embodiments thereof. In one such automated embodiment, diethylphosphoramidites are used as starting materials and may be synthesized as described by Beaucage et al., 1981, *Tetrahedron Letters* 22:1859–1862. One method for synthesizing oligonucleotides on a modified solid support is described in U.S. Pat. No. 4,458,066. One can also use a primer that has been isolated from a biological soume (such as a restfiction endonuclease digest).

No matter what primers are used, however, the reaction mixture must contain a template for PCR to occur, because the specific nucleic acid sequence is produced by using a nucleic acid containing that sequence as a template. The first step involves contacting each nucleic acid strand with four different nucleoside triphosphates and one oligonucleotide primer for each strand of each specific nucleic acid sequence being amplified or detected. If the nucleic acids to be amplified or detected are DNA, then the nucleoside triphosphates are usually dATP, dCTP, dGTP, and dTTP, although various nucleotide derivatives can also be used in the process. The concentration of nucleotide triphosphates can vary widely. Typically the concentration is 50–200 μM in each dNTP in the buffer for amplification, and $MgCl_2$ is present in the buffer in an amount of 1 to 3 mM to activate the polymerase and ihcrease the specificity of the reaction. However, dNTP concentrations of 1–20 μM may be preferred for some applications, such as DNA sequencing.

The nucleic acid strands of the target nucleic acid serve as templates for the synthesis of additional nucleic acid strands, which are extension products of the primers. This synthesis can be performed using any suitable method, but generally occurs in a buffered aqueous solution, preferably at a pH of 7 to 9, most preferably about 8. To facilitate synthesis, a molar excess of the two oligonucleotide primers is added to the buffer containing the template strands. As a practical matter, the amount of primer added will generally be in molar excess over the amount of complementary strand (template) when the sequence to be amplified is contained in a mixture of complicated long-chain nucleic acid strands. A large molar excess is preferred to improve the efficiency of the process. Accordingly, primer:template ratios of about 1000:1 are generally employed for cloned DNA templates, and primer:template ratios of about $10^8$:1 are generally employed for amplification from complex genomic samples.

The mixture of template, primers, and nucleoside triphosphates is then treated according to whether the nucleic acids being amplified or detected are double- or single-stranded. If the nucleic acids are single-stranded, then no denaturation step need be employed, and the reaction mixture is held at a temperature which promotes hybridization of the primer to its complementary target (template) sequence. Such temperature is generally from about 35° C. to 65° C. or more, preferably about 37°–60° C. for an effective time, generally from a few seconds to five minutes, preferably from 30 seconds to one minute. A hybridization temperature of 35°–80° C. may be used for TZ05 DNA polymerase, and 15-mer or longer primers are used to increase the specificity of primer hybridization. Shorter primers require lower hybridization temperatures or agents which stabilize double-stranded DNA.

The complement to the original single-stranded nucleic acids can be synthesized by adding TZ05 DNA polymerase in the presence of the appropriate buffer, dNTPs, and one or more oligonucleotide primers. If an appropriate single primer is added, the primer extension product will be complementary to the single-stranded nucleic acid and will be hybridized with the nucleic acid strand in a duplex of strands of equal or unequal length (depending where the primer hybridizes on the template), which may then be separated into single strands as described above to produce two single, separated, complementary strands. Alternatively, two or more appropriate primers (one of which will prime synthesis using the extension product of the other primer as a template) may be added to the single-stranded nucleic acid and the reaction carried out.

If the nucleic acid contains two strands, as in the case of amplification of a double-stranded target or second-cycle amplification of a single-stranded target, the strands of nucleic acid must be separated before the primers are hybridized. This strand separation can be accomplished by any suitable denaturing method, including physical, chemical or enzymatic means. One preferred physical method of separating the strands of the nucleic acid involves heating the nucleic acid until complete (>99%) denaturation occurs. Typical heat denaturation involves temperatures ranging from about 90° to 105° C. for times generally ranging from about a few seconds to 4 minutes, depending on the composition and size of the nucleic acid. Preferably, the effective denaturing temperature is 90°–100° C. for a few seconds to 1 minute. Strand separation may also be induced by an enzyme from the class of enzymes known as helicases or the enzyme RecA, which has helicase activity and in the presence of riboATP is known to denature DNA. The reaction conditions suitable for separating the strands of nucleic acids with helicases are described by Kuhn Hoffmann-Bering, 1978, *CSH-Quantitative Biology* 43:63, and techniques for using RecA are reviewed in Redding, 1982, *Ann. Rev. Genetics* 16:405–437. The denaturelion produces two separated complementary strands of equal or unequal length.

If the double-stranded nucleic acid is denatured by heat, the reaction mixture is allowed to cool to a temperature which promotes hybridization of each primer to the complementry target (template) sequence. This temperature is usually from about 35° C. to 65° C. or more, depending on reagents, preferably 37°–60° C. The hybridization temperature is maintained for an effective time, generally 30 seconds to 5 minutes, and preferably 1–3 minutes. In practical terms, the temperature is simply lowered from about 95° C. to as low as 37° C., and hybridization occurs at a temperature within this range.

Whether the nucleic acid is single- or double-stranded, the DNA polymerase from Thermus species Z05 may be added at the denaturation step or when the temperature is being reduced to or is in the range for promoting hybridization. Although the thermostability of TZ05 polymerase allows one to add TZ05 polymerase to the reaction mixture at any time, one can substantially inhibit non-specific amplification by adding the polymerase to the reaction mixture at a point in time when the mixture will not be cooled below the stringent hybridization temperature. After hybridization, the reaction mixture is then heated to or maintained at a temperature at which the activity of the enzyme is promoted or optimized, i.e., a temperature sufficient to increase the activity of the enzyme in facilitating synthesis of the primer extension products from the hybridized primer and template. The temperature must actually be sufficient to synthesize an extension product of each primer which is complementary to each nucleic acid template, but must not be so high as to denature each extension product from its complementary template (i.e., the temperature is generally less than about 80°–90° C.).

Depending on the nucleic acid(s) employed, the typical temperature effective for this synthesis reaction generally ranges from about 40° to 80° C., preferably 50°–75° C. The temperature more preferably ranges from about 65°–75° C. for Thermus species Z05 DNA polymerase. The period of time required for this synthesis may range from several seconds to 40 minutes or more, depending mainly on the temperature, the length of the nucleic acid, the enzyme, and the complexity of the nucleic acid mixture. The extension time is usually about 30 seconds to three minutes. If the nucleic acid is longer, a longer time period is generally required for complementary strand synthesis. The newly synthesized strand and the complement nucleic acid strand form a double-stranded molecule which is used in the succeeding steps of the amplification process.

In the next step, the strands of the double-stranded molecule are separated by heat denaturation at a temperature and for a time effective to denature the molecule, but not at a temperature and for a period so long that the thermostable enzyme is completely and irreversibly denatured or inactivated. After this denaturation of template, the temperature is decreased to a level which promotes hybridization of the primer to the complementary single-stranded molecule (template) produced from the previous step, as described above.

After this hybridization step, or concurrently with the hybridization step, the temperature is adjusted to a temperature that is effective to promote the activity of the thermostable enzyme to enable synthesis of a primer extension product using as a template both the newly synthesized and the original strands. The temperature again must not be so high as to separate (denature) the extension product from its template, as described above. Hybridization may occur during this step, so that the previous step of cooling after denaturation is not required. In such a case, using simultaneous steps, the preferred temperature range is 50°–70° C.

The heating and cooling steps involved in one cycle of strand separation, hybridization, and extension product synthesis can be repeated as often as needed to produce the desired quantity of the specific nucleic acid sequence. The only limitation is the amount of the primers, thermostable enzyme, and nucleoside triphosphates present. Usually, from 15 to 30 cycles are completed. For diagnostic detection of amplified DNA, the number of cycles will depend on the nature of the sample and the sensitivity of the detection process used after amplification. If the sample is a complex mixture of nucleic acids, more cycles will usually be required to amplify the signal sufficiently for detection. For general amplification and detection, the process is repeated about 15 times. When amplification is used to generate sequences to be detected with labeled sequence-specific probes and when human genomic DNA is the target of amplification, the process is usually repeated 15 to 30 times to amplify the sequence sufficiently that a clearly detectable signal is produced, i.e., so that background noise does not interfere with detection.

No additional nucleotides, primers, or thermostable enzyme need be added after the initial addition, provided that no key reagent has been exhausted and that the enzyme has not become denatured or irreversibly inactivated, in which case additional polymerase or other reagent would have to be added for the reaction to continue. Addition of such materials at each step, however, will not adversely affect the reaction. After the appropriate number of cycles has been completed to produce the desired amount of the specific nucleic acid sequence, the reaction may be halted in the usual manner, e.g., by inactiveting the enzyme by adding EDTA, phenol, SDS, or $CHCl_3$ or by separating the components of the reaction.

The amplification process may be conducted continuously. In one embodiment of an automated process, the reaction mixture may be temperature cycled such that the temperature is programmed to be controlled at a certain level for a certain time. One such instrument for this purpose is the automated machine for handling the amplification reaction manufactured and developed by Hoffmann-La Roche Inc. and marketed through Perkin-Elmer (Norwalk, Conn.). Detailed instructions for carrying out PCR with the instrument are available upon purchase of the instrument.

TZ05 DNA polymerase is very useful in the diverse processes in which amplification of a nucleic acid sequence by the polymerase chain reaction is useful. The amplification method may be utilized to clone a particular nucleic acid sequence for insertion into a suitable expression vector, as described in U.S. Pat. No. 4,800,159. The vector may be used to transform an appropriate host organism to produce the gene product of the sequence by standard methods of recombinant DNA technology. Such cloning may involve direct ligation into a vector using blunt-end ligation, or use of restriction enzymes to cleave at sites contained within the primers or amplified target sequences. Other processes suitable for TZ05 polymerase include those described in U.S. Pat. Nos. 4,683,194; 4,683,195; and 4,683,202 and European Patent Publication Nos. 229,701; 237,362; and 258,017; these patents and publications are incorporated herein by reference. In addition, the present enzyme is useful in asymmetric PCR (see Gyllensten and Erlich, 1988, *Proc. Natl. Acad. Sci. U.S.A.* 85:7652–7656, incorporated herein by reference); inverse PCR (Ochman et al., 1988, *Genetics* 120:621, incorporated herein by reference); and for DNA sequencing (see Innis et al., 1988, *Proc. Natl. Acad. Sci. U.S.A.* 85:9436–9440, and McConlogue et al., 1988, *Nuc. Acids Res.* 16(20):9869). TZ05 polymerase is also believed to have reverse transcriptase activity, (see copending Ser. No. 455,611, filed Dec. 22, 1989, and in the continuation-in-part of that application, Ser. No. 585,471, filed Sep. 20, 1990, both of which are incorporated herein by reference), and 5'→3' exonuclease activity (also known as structure dependent single strand exonuclease (SDSSE) activity).

The reverse transcriptase activity of the TZ05 DNA polymerase permits this enzyme to be used in methods for transcribing and amplifying RNA. The improvement of such methods resides in the use of a single enzyme, whereas previous methods have required more than one enzyme.

The improved methods comprise the steps of: (a) combining an RNA template with a suitable primer under conditions whereby the primer will anneal to the corresponding RNA template; and (b) reverse transcribing the RNA template by incubating the annealed primer-RNA template mixture with TZ05 DNA polymerase under conditions sufficient for the DNA polymerase to catalyze the polymerization of deoxyribonucleotide triphosphates to form a DNA sequence complementary to the sequence of the RNA template.

In another aspect of the above method, the primer which anneals to the RNA template may also be suitable for use in a PCR amplification. In PCR, a second primer which is complementary to the reverse transcribed cDNA strand provides a site for initiation of synthesis of an extension product. As already discussed above, the TZ05 DNA polymerase is able to catalyze this extension reaction on the cDNA template.

In the amplification of an RNA molecule by TZ05 DNA polymerase, the first extension reaction is reverse transcription, and a DNA strand is produced as an RNA/cDNA hybrid molecule. The second extension reaction, using the DNA strand as a template, produces a double-stranded DNA molecule. Thus, synthesis of a complementary DNA strand from an RNA template with TZ05 DNA polymerase provides the starting material for amplification by PCR.

When TZ05 DNA polymerase is used for nucleic acid transcription from an RNA template, buffers which contain $Mn^{2+}$ may provide improved stimulation of TZ05 reverse transcriptase activity compared to $Mg^{2+}$-containing reverse transcription buffers. Consequently, increased cDNA yields may also result from these methods.

As stated above, the product of RNA transcription by TZ05 DNA polymerase is an RNA/cDNA hybrid molecule. The RNA can be removed or separated from the cDNA by heat denaturation or any number of other known methods including alkali, heat or enzyme treatment. The remaining cDNA strand then serves as a template for polymerization of a complementary strand, thereby providing a means for obtaining a double-stranded cDNA molecule suitable for amplification or other manipulation. The second strand synthesis requires a sequence specific primer and TZ05 DNA polymerase.

Following the synthesis of the second cDNA strand, the resultant double-stranded cDNA molecule can serve a number of purposes including DNA sequencing, amplification by PCR or detection of a specific nucleic acid sequence. Specific primers useful for amplification of a segment of the cDNA can be added subsequent to the reverse transcription. Also, it may be desirable to use a first set of primers to synthesize a specific cDNA molecule and a second nested set of primers to amplify a desired cDNA segment. All of these reactions are catalyzed by TZ05 DNA polymerase.

TZ05 DNA polymerase may also be used to simplify and improve methods for detection of RNA target molecules in a sample. In these methods, TZ05 DNA polymerase catalyzes: (a) reverse transcription; (b) second strand cDNA synthesis; and, if desired (c) amplification by PCR. The use of TZ05 DNA polymerase in the described methods eliminates the previous requirement of two sets of incubation conditions which were necessary due to the use of different enzymes for each step. The use of TZ05 DNA polymerase provides RNA transcription and amplification of the resulting complementary DNA with enhanced specificity and with fewer steps than previous RNA cloning and diagnostic methods. These methods are adaptable for use in laboratory or clinical analysis, and kits for making such analysis simple to perform are an important aspect of the present invention.

The RNA which is transcribed and amplified in the above methods can be derived from a number of sources. The RNA template may be contained within a nucleic acid preparation from an organism such as a viral or bacterial nucleic acid preparation. The preparation may contain cell debris and other components, purified total RNA or puffled mRNA. The RNA template may also be a population of heterogeneous RNA molecules in a sample. Furthermore, the target RNA may be contained in a biological stunpie, and the sample may be a heterogeneous sample in which RNA is but a small portion thereof. Examples of such biological samples include blood samples and biopsied tissue samples.

Although the primers used in the reverse transcription step of the above methods are generally completely complementmy to the RNA template, they need not be. As in PCR, not every nucleotide of the primer must be complementary to the template for reverse transcription to occur. For example, a non-complementary nucleotide sequence may be present at the 5' end of the primer with the remainder of the primer sequence being complementary to the RNA. Alternatively, non-complementary bases can be interspersed into the primer, provided that the primer sequence has sufficient complementarity with the RNA template for hybridization to occur and allow synthesis of a complementary DNA strand.

The SDSSE activity of TZ05 DNA polymerase may limit the amount of product produced by PCR and create a plateau phenomenon in the normally exponential accumulation of product. The SDSSE activity may also limit the size of the PCR product produced and the ability to generate PCR product from GC-rich target template. The SDSSE activity can also be important in assays such as those described in Ser. No. 563,758, filed Aug. 6, 1990, incorporated herein by reference. SDSSE activity relates to the hydrolysis of phosphodiester bonds. SDSSE activity generally excises 5' terminal regions of double-stranded DNA, thereby releasing 5'-mono- and oligonucleotides. The preferred substrate for the SDSSE activity is displaced single-stranded DNA, with hydrolysis of the phosphodiester bond which occurs between the displaced single-stranded DNA and the double-helical DNA. The preferred cleavage site is a phosphorlester bond in the double helical region.

Site-directed mutagenesis or deletion mutagenesis may be utilized to eliminate the SDSSE activity of a polymerase having such activity. Such polymerases are an important aspect of the present invention. For example, a deletion of the first 76 amino acids, creating a protein beginning with Ala 77, is believed to be effective for reducing the SDSSE activity of *Thermus aquaticus* DNA polymerase. Those of skill in the art recognize that when such a deletion mutant is to be expressed in recombinant host cells, a methionine codon is usually placed at the 5' end of the coding sequence, so that the amino-terminal sequence of the deletion mutant protein would be MET-ALA. Alanine 77 is found within the sequence HEAYG in Taq DNA polymerase. A similar sequence motif HEAYE is found in Tth, TZ05, and Tsps17 DNA polymerases. For TZ05 DNA polymerase, the corresponding alanine in this motif is Ala 78. A deletion up to the alanine in the motif HEAY(G/E) in any thermostable DNA polymerase containing this sequence can reduce or eliminate the SDSSE activity.

Furthermore, a site-directed mutation of G to A in the second position of the codon for Gly at residue 46 in the Taq DNA polymerase sequence has been found to result in an approximately 100-fold reduction of SDSSE activity with no apparent change in polymerase activity, processivity or extension rate. This site-directed mutation of the Taq DNA polymerase nucleotide sequence results in an amino acid change of Gly (46) to Asp. Glycine 46 is conserved in Thermus species Z05 DNA polymerase, and the same Gly (46) to Asp mutation would have a similar effect on TZ05 SDSSE activity.

Gly 46 is found in a conserved AVYGF sequence domain, and changing the glycine to aspartic acid within this conserved sequence domain of any DNA polymerase is also expected to alter SDSSE activity. In addition, a deletion of all amino terminal amino acids up to and including the glycine in the AVYGF domain will also alter the SDSSE activity of any thermostable DNA polymerase having this sequence domain, inchding the DNA polymerase of Thermus species sps17.

The following examples are offered by way of illustration only and are by no means intended to limit the scope of the claimed invention. In these examples, all percentages are by weight if for solids and by volume if for liquids, unless otherwise noted, and all temperatures are given in degrees Celsius.

Example 1

Purification of Thermus Species Z05 DNA Polymerase

This example describes the isolation of TZ05 DNA polymerase from Thermus species Z05.

Thermus species Z05 cells are grown in flasks in the following medium, adjusted to pH 8.0 with ammonium hydroxide: sodium citrate, 1 mM; potassium phosphate, pH 7.9, 5 mM; ammonium chloride, 10 mM; magnesium sulfate, 0.2 mM; calcium chloride, 0.1 mM; sodium chloride, 1 g/l; yeast extract 1 g/l; tryptone, 1 g/l; glucose, 2 g/l; and ferrous sulfate, 0.01 mM.

The cells are cultured overnight at 70° C., and 600 ml from the flask is used to inoculate 10 liters of the same medium in a fermentor. The fermentor operates with dissolved oxygen at 40%, a temperature of 70° C. and a stirring rate of 400 rpm.

The above culture of the T. species Z05 cells is harvested by centrifugation after nine hours of cultivation, in late log phase, at a cell density of 1.4 g dry weight/l. Twenty grams of cells are resuspended in 80 ml of a buffer consisting of 50 mM Tris HCl pH 7.5, 0.1 mM EDTA. The cells are lysed and the lysate is centrifuged for two hours at 35,000 rpm in a Beckman TI 45 rotor at 4° C. The supernatant is collected (fraction A) and the protein fraction precipitating between 45 and 75% saturation of ammonium sulfate is collected, dissolved in a buffer consisting of 0.2M potassium phosphate buffer, pH 6.5, 10 mM 2-mercaptoethanol, and 5% glycerine, and finally dialyzed against the same buffer to yield fraction B.

Fraction B is applied to a 2.2×30 cm column of DEAE-cellulose, equilibrated with the above described buffer. The column is then washed with the same buffer and the fractions containing protein (determined by absorbance at 280 nM) are collected. The combined protein fraction is dialyzed against a second buffer, containing 0.01M potassium phosphate buffer, pH 7.5, 10 mM 2-mercaptoethanol, and 5% glycerine, to yield fraction C.

Fraction C is applied to a 2.6×21 cm column of hydroxyapatite, equilibrated with a second buffer. The column is then washed and the enzyme is eluted with a linear gradient of 0.01–0.5M potassium phosphate buffer, pH 7.5, containing 10 mM 2-mercaptoethanol and 5% glycerine. Fractions containing DNA polymerase activity (90–180 mM potassium phosphate) are combined, concentrated four-fold using an Amicon stirred cell and YM 10 membrane, and dialyzed against the second buffer to yield fraction D.

Fraction D is applied to a 1.6×28 cm column of DEAE-cellulose, equilibrated with the second buffer. The column is washed and the polymerase is eluted with a linear gradient of 0.01–0.5M potassium phosphate in the second buffer. The fractions are assayed for contaminating endonuclease(s) and exonuclease(s) by electrophoretically detecting the change in molecular weight of phage λ DNA or supercoiled plasmid DNA after incubation with an excess of DNA polymerase (for endonuclease) and after treatment with a restriction enzyme that cleaves the DNA into several fragments (for exonuclease). Only those DNA polymerase fractions having minimal nuclease contamination are pooled. To the pool is added autoclaved gelatin in an amount of 250 µg/ml, and dialysis is conducted against the second buffer to yield Fraction E.

Fraction E is applied to a phosphocellulose column and eluted with a 100 ml gradient (0.01–0.4M KCl gradient in 20 mM potassium phosphate buffer pH 7.5). The fractions are assayed for contaminating endo/exonuclease(s) as described above as well as for polymerase activity (by the method of Kaledin et al.) and then pooled. The pooled fractions are dialyzed against the second buffer, and then concentrated by dialysis against 50% glycerine and the second buffer to yield the desired polymerase.

Example 2

Isolation of DNA Fragments Encoding TZ05 DNA Polymerase

This Example presents a degenerate primer method used to isolate DNA fragments that encode TZ05 DNA polymerase. In this method, various sets of forward and reverse primers were used in the polymerase chain reaction. These primers were designed to hybridize with nucleic acids that encode various motifs in the template binding domains of thermostable DNA polymerases.

Two methods were used to determine which degenerate primer sets produced correct regions of the TZ05 polymerase gene. The products were identified as correct either by DNA sequence analysis or by restriction analysis in which several restriction sites present in the Taq polymerase gene were also present in the TZ05 product. In addition, the products were identified as distinct from Taq DNA polymerase gene sequences by the presence (or absence) of restriction sites not in (or present in) the Taq gene sequence. The degenerate primer sets which produced correct regions of the TZ05 polymerase gene are listed below in Table 1. If more than one set of primers were used in the pool, each set is indicated below.

TABLE 1

Degenerate Primer Sets That Produced Correct Regions of TZ05 Polymerase Gene

| Forward Primer Sequence | | Reverse Primer Sequence | |
|---|---|---|---|
| DG157 | Gln Asn Ile Pro Val<br>5'CGAGATCTCARAAYATHCCSGT | DG169 | 5'CGGAATTCGTYTCNACRTASCC<br>Thr Glu Val Tyr Gly |
| DG157 | Gln Asn Ile Pro Val<br>5'CGAGATCTCARAAYATHCCSGT | DG174 | 5'CGGAATTCATRCGYTCSGC<br>Met Arg Glu Ala |
| MK143 | Ala Val Leu Ala His Met<br>5'CCGCTGTCCTGGCCCACATG | MK131 | 5'CCCGGATCAGGTTCTCGTC<br>Arg Ile Leu Asn Glu Asp |
| DG140–DG141 | Ala His Met Glu Ala<br>5'CGAGATCTGCNCAYATGGAAGC | MK131 | 5'CCCGGATCAGGTTCTCGTC<br>Arg Ile Leu Asn Glu Asp |
|  | Ala His Met Glu Ala<br>5'CGAGATCTGCNCAYATGGAGGC |  |  |
| DG152–DG153 | Glu Ala Asp Asp Val<br>5'CGAGATCTGARGCNGAYGATGT | DG148–DG149 | 5'CGGAATTCGCCGTYTTYTCWCC<br>Ala Thr Lys Glu Gly |
|  | Glu Ala Asp Asp Val<br>5'CGAGATCTGARGCNGAYGACGT |  | 5'CGGAATTCGCNGTYTTYTCSCC<br>Ala Thr Lys Glu Gly |
| DG150–DG151 | Val Phe Asp Ala Asn Lys<br>5'CGAGATCTGTNTTYGAYGCWAA | DG148–DG149 | 5'CGGAATTCGCNGTYTTYTCWCC<br>Ala Thr Lys Glu Gly |
|  | Val Phe Asp Ala Asn Lys<br>5'CGAGATCTGTNTTYGAYGCSAA |  | 5'CGGAATTCGCNGTYTTYTCSCC<br>Ala Thr Lys Glu Gly |
| DG96–DG97 | Asp Asn Leu Pro Gly<br>5'CGAGATCTGAYAAYYTRCCSGG | DG138–DG139 | 5'CACGGAATTCYTCWCCYTC<br>Glu Glu Gly Glu Asp |

TABLE 1-continued

Degenerate Primer Sets That Produced Correct Regions of TZ05 Polymerase Gene

| Forward Primer Sequence | Reverse Primer Sequence |
|---|---|
| Asp Asn Leu Pro Gly<br>5'CGAGATCTGAYAAYYTRCCWGG | 5'CACGGAATTCYTCSCCYTC<br>Glu Glu Gly Glu |
| DG164–DG167 Gly Tyr Val Glu Thr<br>5'CGAGATCTGGNTAYGTWGAAAC | DG181–DG182 5'CGGAATTCNGCNGCNGTSCCYTG<br>Asp Ala Ala Thr Gly Gln<br>Glu |
| Gly Tyr Val Glu Thr<br>5'CGAGATCTGGNTAYGTWGAGAC | 5'CGGAATTCNGCNGCNGTWCCYTG<br>Asp Ala Ala Thr Gly Gln<br>Glu |
| Gly Tyr Val Glu Thr<br>5'CGAGATCTGGNTAYGTSGAAAC | |
| Gly Tyr Val Glu Thr<br>5'CGAGATCTGGNTAYGTSGAGAC | |
| DG164–DG167 Gly Tyr Val Glu Thr<br>5'CGAGATCTGGNTAYGTWGAAAC | DG160–DG163 5'CGGAATTCRTCRTGWACCTG<br>Glu Asp His Val Gln<br>Asp |
| Gly Tyr Val Glu Thr<br>5'CGAGATCTGGNTAYGTWGAGAC | 5'CGGAATTCRTCRTGWACTTG<br>Glu Asp His Val Gln<br>Asp |
| Gly Tyr Val Glu Thr<br>5'CGAGATCTGGNTAYGTSGACAC | 5'CGGAATTCRTCRTGSACCTG<br>Glu Asp His Val Gln<br>Asp |
| Gly Tyr Val Glu Thr<br>5'CGAGATCTGGNTAYGTSGAGAC | 5'CGGAATTCRTCRTGSACTTG<br>Glu Asp His Val Gln<br>Asp |

In Table 1, A is Adenine; C is Cytidine; G is Guanidine; T is Thymine; Y is C+T (pYrimidine); S is G+C (Strong interaction; three hydrogen bonds); W is A+T (Weak interaction; two hydrogen bonds); N is A+C+G+T (aNy); and R is G+A (puRine). In the examples below, where a forward or a reverse primer is indicated as "DGXX-DGXX" or "DGXX/DGXX," one should assume that all of the primers between the two XX numbers shown were used as the forward or reverse primer. All of the primer sets discussed below are shown in the table above.

From the table, one should note that all of the primers encode a restriction site at the 5' end of the primer to facilitate cloning and that the amino acid sequences shown for the reverse primers are encoded by a sequence complementary to the primer.

When the above degenerate primer sets were used in the PCR to amplify regions of the TZ05 polymerase gene, the following reaction conditions were used: 10 mM Tris, pH 8.3; 50 mM KCl; 1.5 mM $MgCl_2$; gelatin; 200 μM each dNTP; 10 ng chromosomal DNA at $4.7 \times 10^6$ base pairs equivalent to $5.15 \times 10^{-18}$ g/chromosome or $3.2 \times 10^{-14}$ M; 500 nM each oligo primer set; and 2.5–5 units of Taq polymerase.

The temperature cycle for the PCR was 5 cycles of: 1.5 minutes at 45° C., a 2 minute ramp to 98° C., and then 45 seconds at 98° C.; followed by 30 cycles of: 50° C. for 2 minutes, a step to 98° C., and then 45 seconds at 98° C. The PCR products generated were then chloroform extracted to remove oil, desalted over a biogel P-4 spin column and restricted with the indicated restriction enzyme according to the manufacturer's specifications.

The PCR products were analyzed on 10% polyacrylamide gels using MspI-digested plasmid pBR322 as a molecular weight standard. Undigested PCR products were also included on the gel analysis to indicate contaminating PCR products which might confuse the digestion analysis. In some instances, the restriction analysis was performed on reamplified, gel-purified PCR products.

Listed below are the results for the various degenerate primer sets that produced correct regions of the TZ05 polymerase gene (see Tables 1A–1G). The numbers in each table below represent the size, in base pairs, determined from the confirmed sequence ("expected") or experimental data ("experimental").

TABLE A

Primer Set DG157/DG169
To obtain the results in this table, chromosomal DNA was amplified with the listed primer set, and the PCR product was directly analyzed by restriction analysis.

| | Taq | | Z05 | |
|---|---|---|---|---|
| Enzyme | Expected | Experimental | Expected | Experimental |
| Undigested | 438 | 438 | 438 | 450 |
| StuI | 336 | 330 | 438 | 450 |
| | 102 | 107 | | |
| SmaI | 222 | 229 | 438 | 435 |
| | 216 | 215 | | |
| SacI | 328 | 310 | 328 | 310 |
| | 110 | 127 | 110 | 127 |

TABLE 1B

Primer Set MK143/MK131
To obtain the results in this table, chromosomal DNA was amplified with the listed primer set, and the PCR product was directly analyzed by restriction analysis.

| Enzyme | Taq Expected | Taq Experimenal | Z05 Expected | Z05 Experimental |
|---|---|---|---|---|
| Undigested | 579 | | 579 | |
| SacI | 298 | 335 | 229 | 312 |
|  | 234 | 280 | 234 | 260 |
|  | 46 | 58 | 46 | 54 |
| BamHI | 467 | 450 | 467 | 450 |
|  | 111 | 128 | 111 | 128 |
| PstI | 292 | 298 | 430 | 450 |
|  | 287 | 284 | 148 | 175 |

TABLE 1C

Primer Set DG140-DG141/MK131
The results in this Table were obtained from an analysis which consisted of two series of PCR. First, chromosomal DNA was amplified with an external set of primers (DG136-DG137 to DG168-DG169), from which no visible product was detectable. Then, 1:1000 and 1:100 of the above reaction were reamplified directly with the primer combination DG140-DG141 to MK131, and the product thereof was analyzed directly by restriction digestion.

| Enzyme | Taq Expected | Taq Experimenal* | Z05 Expected | Z05 Experimental |
|---|---|---|---|---|
| Undigested | 576 | | 579 | |
| SacI | 301 | 297 | 301 | 300 |
|  | 234 | 245 | 234 | 245 |
|  | 46 | 55 | 46 | 55 |
| BamHI | 470 | 435 | 470 | 430 |
|  | 111 | 126 | 111 | 120 |
| PstI | 292 | 292 | 433 | 440 |
|  | 284 | 283 | 148 | 155 |

*average from the two determinations

TABLE 1D

Primer Set DG152-DG153/DG148-DG149
To obtain the results in this Table, chromosomal DNA was originally amplified with the listed primers. The PCR products werd extracted with chloroform, phenol/chloroform, and ether, desalted over a biogel P-4 spin column and electrophoresed on a 3% NuSieve ™ GTG low melting agarose gel. The desired band was cut out of the gel, extracted first with phenol and then with ether, and desalted over a biogel P-4 spin column. A sample of the purified band was reamplified with the listed primers, and the products of this latter PCR were used in the restriction analysis.

| Enzyme | Taq Expected | Taq Experimenal | Z05 Expected | Z05 Experimental |
|---|---|---|---|---|
| Undigested | 279 | 320 | 279 | 300 |
| ApaI | 210 | 230 | 279 | 280 |
|  | 69 | 80 | | |
| BanI | 141 | 150 | 279 | 280 |
|  | 138 | 140 | | |
| KpnI | 141 | 150 | 279 | 280 |
|  | 138 | 140 | | |
| SmaI | 242 | 252 | 242 | 235 |
|  | 37 | 39 | 37 | 40 |
| XhoI | 279 | 280 | 279 | 275 |

TABLE 1E

Primer Set DG150-DG151/DG148-DG149
The same procedure as set forth above in Table 1D was also used to obtain the results in this Table.

| Enzyme | Taq Expected | Taq Experimenal | Z05 Expected | Z05 Experimental |
|---|---|---|---|---|
| Undigested | 435 | 430 | 435 | 430 |
| ApaI | 294 | 300 | 435 | 430 |
|  | 72 | 76 | | |
|  | 69 | | | |
| BanI | 297 | 302 | 435 | 430 |
|  | 138 | 145 | | |
| KpnI | 297 | 300 | 435 | 430 |
|  | 138 | 143 | | |
| SmaI | 242 | 250 | 398 | 400 |
|  | 157 | 168 | 37 | 46 |
|  | 37 | 39 | | |
| XhoI | 286 | 300 | 286 | 295 |
|  | 149 | 160 | 149 | 167 |

TABLE 1F

Primer Set DG164-DG167/DG181-DG182
The same procedure as set forth above in Table 1D was also used to obtain the results in this Table.

| Enzyme | Taq Expected | Taq Experimental | Z05 Expected | Z05 Experimental |
|---|---|---|---|---|
| Unretricted | 139 | 160 | 139 | 167 |
| AvaI | 76 | 86 | 76 | 96 |
|  | 63 | 73 | 63 | 9 |
| BanI | 122 | 150 | 122 | 157 |
|  | 17 | 18 | 17 | 18 |
| HpaII | 76 | 91 | 76 | 88 |
|  | 63 | 72 | 63 | 74 |
| MboII | 63 | 60 | 59 | 73 |
|  | 59 | 58 | 37 | 45 |
|  | 17 | 18 | 26 | 29 |
|  | 17 | 18 | | |
| SmaI | 76 | 91 | 76 | 89 |
|  | 63 | 72 | 73 | 73 |

TABLE 1G

Primer Set DG164-DG167/DG160-DG167
The same procedure as set forth above in Table 1D was also used to obtain the results in this Table.

| Enzyme | Taq Expected | Taq Experimental | Z05 Expected | Z05 Experimental |
|---|---|---|---|---|
| Unretricted | 220 | 212 | 220 | 235 |
| AvaI | 157 | 170 | 157 | 172 |
|  | 63 | 74 | 63 | 78 |
| BanI | 122 | 130 | 122 | 138 |
|  | 98 | 106 | 98 | 114 |
| HpaII | 157 | 166 | 111 | 130 |
|  | 63 | 70 | 66 | 77 |
|  | 46 | 58 | | |
| MboII | 72 | 77 | 72 | 83 |
|  | 68 | 58 | 68 | 44 |
|  | 63 | 18 | 37 | 29 |
|  | 17 | 26 | 22 | |
|  | 17 | 18 | | |
| SmaI | 157 | 170 | 157 | 188 |
|  | 63 | 71 | 63 | 80 |

Example 3

Cloning the Thermus Species Z05 (TZ05) DNA Polymerase I Gene

This Example describes the strategy and methodology for cloning the TZ05 DNA polymerase (TZ05 Pol) gene of Thermus species Z05.

I. Cloning PCR Products

A. MK131 and MK143 (clones 12-5, 12-14, 12-18)

1. Initial PCR reaction

Chromosomal DNA (10 mg) from Thermus species Z05 was amplified as described above in Example 2 using the primers MK131 and MK143 (50 pmoles each). Amplification of the correct product was confirmed by comparing restriction digests of the amplified products to similar products using Taq chromosomal DNA as shown in Table 1B. The digestion patterns of both products were identical using SacI (298 bp, 234 bp, and 46 bp based on final sequence) and BamHI (467 bp and 111 bp based on final sequence) restriction endonucleases but differed using PstI (430 bp and 148 bp, for TZ05 based on final sequence). The desired PCR product was purified following electrophoresis of one-fifth of the PCR reaction on a 10% polyacrylamide gel. Due to the low yield and presence of several bands in the initial PCR, a second amplification was performed with one-fiftieth of the purified fragment and 50 pmoles each of MK131 and MK143.

2. PreparatiOn of the fragment for cloning

The final PCR product was extracted with chloroform and then with phenol/chloroform, and then desalted over a biogel P-4 spin column. To ensure the fragment had blunt ends, the preparation was treated with E. coli DNA polymerase I, Klenow fragment, according to the manufacturer's specification, and then extracted with phenol/chloroform and ether. The product was then concentrated and desalted over a biogel P-4 spin column. Because the primers MK131 and MK143 lacked 5' phosphates, the preparation was phosphorylated by treatment with T4 polynucleotide kinase and $\gamma$-$^{32}$P-ATP, according to the manufacturer's specifications, extracted with phenol/chloroform and then with ether, and concentrated and desalted over a biogel P-4 spin column.

3. Preparation of a vector for cloning

Vector pBSM13+HindIII::BglII (10 µg) was restricted with the restriction enzyme SmaI (30 units at room temperature for 2.5 hours) followed by dephosphorylation using bacterial alkaline phosphatase (at 37° C. for 1 hour). The preparation was extracted first with phenol/chloroform, then with ether, and then concentrated and desalted over a biogel P-4 spin column. Vector pBSM13+HindIII::BglII was itself constructed from vector pBSM13+ by digesting pBSM13+ with HindIII, blunting the ends of the digested vector by Klenow treatment, ligating BglII linkers (5'-CAGATCTG), transforming host cells, and selecting transformants which contained a plasmid identical to pBSM13+ but for the absence of a HindIII site and the presence of a BglII site.

4. Ligation and screening

The prepared vector (0.4 µg) was ligated to one-eighth of the prepared PCR product using T4 DNA ligase (400 units) and T4 RNA ligase (10 units) at 10° C. for 11 hours. The ligation mixture was transformed into DG98, the transformants were selected on ampicillin-containing media plates, and twenty ampicillin-resistant colonies were grown and then screened by restriction enzyme digestion. Restriction with EcoRI and BglII indicated three potential clones (designated 12-5, 12-14 and 12-18).

Identity was further confirmed by restriction enzyme digestion of the candidate vectors with SacI, which gave the expected restriction fragments when compared to the mapping of the PCR product and demonstrated that clones 12-5 and clones 12-18 were in one orientation and clone 12-14 was in the opposite orientation.

B. DG140–DG141 and MK131 (clones 18-5, -9, -12, -18 and -19)

1. Initial PCR

Thermus species Z05 chrmosomal DNA (10 ng) was initially amplified using DG136/DG137 and DG168/DG169 (50 pmoles each) yielding a series of products. The expected 922 base pair product based on the Taq sequence was not clearly evident). A sample of the PCR product (1/100 and 1/1000) was amplified using DG140/DG141 and MK131 (50 pmoles each). The identity of the major product was confirmed by restriction enzyme digestion using SacI, BamHI and PstI restriction endonucleases. SacI (301 bp, 234 bp and 46 bp based on final sequence) and BamHI (470 bp and 111 bp based on final sequence) gave identical patterns to the Taq product but PstI (433 bp and 148 bp based on final sequence) gave a unique pattern.

2. Preparation of the fragments for cloning

The fragments were prepared as described above for MK131 and MK143 (Example A.2.).

3. Preparation of a vector

Vector pBSM13+HindIII::BglII (10 µg) was restricted with 30 units of SmaI at room temperature for 1 hour followed by restriction with 16 units of BglII at 37° C. for 2.5 hours. The ends were dephosphorylated by treatment first with bacterial alkaline phosphatase at 37° C. for 1 hour. The sample was extracted first with phenol/chloroform and then with ether and dephosphorylated over a biogel P-4 spin column.

4. Ligation and screening

The prepared vector (0.3 µg) was ligated to the prepared PCR product (one-fifth) using 400 units of T4 DNA ligase and 10 units of T4 RNA ligase at 10° C. for 14 hours followed by transformation into DG98 and selection of transformants on ampicillin-containing media plates. Plasmids from twenty ampicillin-resistant clones were screened by restriction analysis. Digestion with EcoRI and BglII identified 8 candidates (designated 18-5, -7, -9, -10, -12, -16, -18 and -19). The correct clone were further identified by restriction with EcoRI and PstI, and BglII and BamHI.

5. Sequence analysis (clone 18-19)

A 0.1 ml sample of a 10 ml overnight culture was inoculated into 10 ml of R2-7 media with 250 µg/ml methicillin and grown at 37° C. until the $OD_{600}$ reached 0.2. About 1.5 ml of each culture was injected with R408 helper phage at an MOI of 10 and the incubation continued at 37° C. for an additional 4–5 hours. The phage were precipitated by incubation in 0.4M NaCl, 29% PEG (8,000) at 4° C. for 16 hours. Following centrifugation, the pellets were resuspended in 100 µl of 10 mM Tris-HCl, 0.1 mM EDTA, pH 8, phenol extracted, and ethanol precipitated. The DNA was then resuspended in 10 mM Tris-HCl, 0.1 mM EDTA, pH 8, and used for sequencing by the method of Sanger, using the Sequenase™ kit. The restriction sites SacI, BamHI, and PstI predicted from the restriction mapping were present in the sequence.

C. DG157 and DG169 (clone 33-1)

1. Initial PCR reaction

Thermus species Z05 chromosoma DNA (10 ng) was amplified using DG157 and DG169 (50 pmoles each), extracted with chloroform, and desalted over a biogel P-4 spin column. The correct product was purified following electrophoresis on a 1% NuSieve™ GTG low melting agarose gel. The amount of desired product was increased by reamplification of 1/300) and 1/30,000 of the purified fragment with the same primers. The PCR products were extracted with chloroform and then with phenol/chloroform, desalted over a biogel P-4 spin column, restricted with EcoRI and BglII (40 units each at 37° C. for 2 hours), extracted with phenol/chloroform and then with ether, and concentrated and desalted over a biogel P-4 spin column. The desired fragment was purified following electrophoresis on a 1% NuSieve™ GTG agarose gel, extracted with phenol and then with ether, and concentrated and desalted over a biogel P-4 spin column.

2. preparation of fragments for cloning

The fragments were prepared as described above for MK131 and MK143 (Example A.2.).

3. Preparation of a vector

Vector pBSM13+HindIII::BglII (62.5 μg) was digested with BglII (80 units at 37° C. for 3 hours) and then by EcoRI (100 units for 2.5 hours). The preparation was dephosphorylated with bacterial alkaline phosphatase at 37° C. for 4 hours, extracted with phenol/chloroform followed by ether, and desalted over a biogel P-4 spin column.

4. Ligation and screening

The prepared vector (0.4 μg) was ligated with fragment (1/100) using 400 units of T4 DNA ligase at 10° C. for 22 hours and the preparation transformed into DG98. Transformants were selected on ampicillin-containing media plates, and twenty ampicillin-resistant colonies were grown up in liquid broth, and the DNA isolated and analyzed by restriction analysis. Restriction with EcoRI and BglII gave the expected size of insert. The identity of the colones was further confirmed by restriction with BglII and SacI.

5. Sequence analysis

A 0.1 ml sample of a fresh overnight culture was grown in R2-7 media with 250 μg/ml methicillin at 37° C. until an O.D.$_{600}$ of 0.2. The cultures were infected with R408 helper phage at an MOI of 10 and the cultures grown an additional 5 hours at 37° C. Single strand DNA was isolated by precipitating 1.3 ml of supernatant from the centrifugation of 1.5 ml of cells with 0.4M NaCl and 29% PEG (8000) at 4° C. for 16 hours. Following centrifugation, the pellets were resuspended in 100 gl of 10 mM Tris-HCl, 0.1 mM EDTA, pH 8, phenol extracted, ethanol precipitated, and the DNA resuspended in 20 μl of 10 mM Tris-HCl, 0.1 mM EDTA, pH 8. The DNA from clone 33-1 was sequenced by the method of Sanger, using the Sequenase™ kit.

II. Mapping Restriction Sites in the Chromosome

A. DG157 and DG169

1. Preparation of Southern filter

Thermus species Z05 chromosomni DNA (2.9 ng) was digested with restriction endonucleases AatII (2 units), AccI (10 units), BanI (25 units), HindIII (20 units), NheI (4 units), or XmnI (6 units) at 37° C. for 5 hours followed by electrophoresis on a 0.7% agarose gel with radioactively labeled HindIII-digested lambda DNA as a molecular weight marker. The DNA was transferred to GeneTrans™ nitrocellulose paper by capillary action using 400 mM NaOH for 18 hours. The membranes were rinsed in 2×SSC, and DNA was cross-linked to the nitrocellulose using a UV Stratalinker™ 1800 and subjected to prehybridization in 6×SSC, 0.1% SDS, 5×Denhardt's, 50 mM sodium phosphate, pH 7.0 and 210 μg/ml sonicareal calf thymus DNA at 45° C. for 2 hours.

2. Preparation of probe

A gel purified PCR fragment (1/1000) derived from TZ05 using DG169 and DG157 was amplified with the same primers in the presence of 200 μM each of dATP, dCTP and dTTP, 40 μM dGTP and 70 μCi of alpha-$^{32}$P-dGTP. The radioactively labeled PCR product was gel purified lollowing electrophoresis on a 3% NuSieve™ GTG low melting agarose gel, phenol extracted, and ether extracted.

3. Hybridization and wash

The filter was hybridized in 6.25×SSC, 0.1% SDS, 5×Denhardt's, 50 mM sodium phosphate, pH 7.0, and 40 μg/ml carrier sonicated heat-denatured calf thymus DNA with 1.7×10$^6$ CPM of probe at 52° C. for 14 hours. The filter was washed twice at 50° C. for 40 to 150 minutes in 5×SSC, 0.1% SDS, and autoradiographed.

4. Results

The size fragments which hybridized to the amplification product DG157/DG169 are listed below.

| Restriction Enzyme | Size Fragments (base pairs) |
| --- | --- |
| AatII | 4,600, 3,600, 2,850 |
| AccI | 4,750, 2,850 |
| BanI | 2,550 |
| HindIII | 3,050 |
| NheI | 17,000 |
| XmnI | 1,550 |

Because of the low stringency of the wash, some of these fragments may be cross-hybridizing fragments.

The following restriction site positions were derived from the final DNA sequence. The AatII site is at codon 121 in the polymerase DNA sequence. The AccI sites are both located in front of (5') the amino terminal methionine codon of the coding sequence. Two of the BanI sites are located in front of (5') the coding sequence. A third BanI site is in codon 757, around the DG181/DG182 hybridization site. The remaining two BanI sites are after (3') the coding sequence; thus probing should have given a fragment of 2492 bp, consistent with the 2550 bp fragment actually observed. One HindIII site is in front of (5') the coding sequence. The second is in codon 700; thus probing should have given a fragment of 2819 bp, consistent with the 3050 bp fragment observed. There are no NheI sites in the final sequence. The two XmnI sites are in codon 269, between the hybridization sites for DG148/DG149 and DG124/DG125, and in codon 769; thus probing should have given a fragment of 1499 bp, consistent with the 1550 bp fragment observed.

III. Southern Blot of HindIII Digested TZ05 Chromosomal DNA

A. Preparation of nitrocellulose filter

TZ05 chromosomal DNA (20 μg) was digested with HindIII at 37° C. A fraction of the restriction digest (0.17 μg) was electrophoresed on a 0.7% agarose gel. The gel was acid nicked by treatment with 0.25N HCl for 15 minutes, rinsed, denatured by treatment with 0.4M NaOH for 5 minutes, and transferred to GeneTrans™ nitrocellulose filter by capillary action in 40 mM NaOH for 22 hours. The filter was washed in 2×SSC, crosslinked using the Stratlinker™ 1800 UV light box, and treated with prehybridization buffer for 3 hours at 50° C.

1. DG140/DG141 and MK131 a. Preparation of a TZ05 Probe with DG140–DG141 and MK131

TZ05 chromosomal DNA (10 ng) was amplified using DG168/DG169 and DG136/DG137. One-hundredth of the PCR product was then amplified using DG140/DG141 and MK131 with 200 μM each of dCTP, dATP, dTTP, and 40 μM dGTP (50 μCi). The PCR product was extracted with chloroform, desalted over a biogel P-4 spin column, and purified following electrophoresis on a 3% NuSieve™ GTG low melting agarose gel. The fragment was extracted with phenol and then with ether, and concentrated.

b. Hybridizlation and autoradiography

The membranes were hybridized with $4\times10^6$ CPM of probe at 60° C. for 16 hours, washed twice in 5×SSC, 0.1% SDS at 60° C. for 1.3 to 3.7 hours, washed in 1×SSC, 0.1% SDS at 60° C. for 2 hours and autoradiographed.

c. Wash of membrane

The previous probe was removed by boiling the membrane in 0.2×SSC, 0.1% SDS.

2. DG160/DG163 and DG164/DG167 a. preparation of a TZ05 Probe with DG160/DG163 and DG164/DG167

TZ05 chromosomal DNA (10 ng) was amplified with DG160/DG163 and DG164/DG167. The PCR product was extracted with phenol/chloroform, chloroform, and ether, desalted over a biogel P-4 spin column, and the PCR fragment purified following electrophoresis on a 3% NuSieve™ GTG low melting agarose gel. The identity of the fragment was extracted with phenol and then with ether and concentrated and desalted over a biogel P-4 spin column. The identity of the fragment was confirmed by restriction analysis with MboII, AvaI, BanI, HpaII, and SmaI. The PCR product gave similar digestion patterns as the analogous Taq product with AvaI, BanI, MboII, and SmaI but a different pattern with HpaII. To prepare labeled probe, a portion (1/1000) of the purified fragment was amplified with DG164/DG164 and DG160/DG163 in the presence of 200 µM each of dATP, dCTP, and dTTP and 40 µM dGTP (50 µCi). The radioactively labeled fragment was purified following electrophoresis on a 3% NuSieve™ GTG low melting agarose gel, extracted with phenol and then with ether, and concentrated and desalted over a biogel P-4 spin column.

b. Hybridization and autoradiography

The blot was hybridized with $1.65\times10^6$ CPM of probe at 50° C. for 72 hours, washed at 50° C. in 5×SSC, 0.1% SDS for 3.5 hours, then 2×SSC, 0.1% SDS at 50° C. for 2 hours, and autoradiographed.

c. Wash of membrane

The previous probe was removed by boiling the membrane in 0.2×SSC, 0.1% SDS.

3. DG148/DG149 and DG152/DG153 a. Preparation of a TZ05 Probe with DG152/DG153 and DG148/DG149

TZ05 chromosomal DNA (10 ng) was amplified with DG152/DG153 and DG148/DG149. The PCR product was extracted with phenol/chloroform, chloroform, and ether, desalted over a biogel P-4 spin column, and the PCR fragment purified following electrophoresis on a 3% NuSieve™ GTG low melting agarose gel. The fragment was extracted with phenol and then with ether and concentrated and desalted over a biogel P-4 spin column. The identity of the fragment was confirmed by restriction analysis with MboII, AvaI, BanI, HpaII, and SmaI. The PCR product gave similar digestion patterns as the analogous Taq product with XhoI but different pattern with ApaI, BanI, KpnI, and SmaI. To prepare labeled probe, a portion (1/1000) of the purified fragment was amplified with DG148/DG149 and DG152/DG153 in the presence of 200 µM each of dATP, dCTP and dTTP and 40 µM dGTP (50 µCi). The radioactively labeled fragment was purified following electrophoresis on a 3% NuSieve™ GTG low melting agarose gel, extracted with phenol and then ether, and concentrated and desalted over a biogel P-4 spin column.

b. Hybridization and autoradiography

The membrane was hybridized with $1.65\times10^6$ CPM of the purified probe at 50° C. for 20 hours, washed in 5×SSC, 0.1% SDS at 50° C. for 3.3 hours, and autoradiographed.

B. Summary

PCR products corresponding to several regions (DG160/DG163 and DG164/DG167, corresponding to positions 2152 to 2357 of the Taq DNA sequence; DG157 and DG169, corresponding to positions 1744 to 2165 of the Taq DNA sequence; and DG140/DG141 and MK131, corresponding to positions 1324 to 1890 of the Taq DNA sequence) were used as probes in Southern transfers of TZ05 chromosomal DNA digested with AatII, AccI, BanI, HindIII, NheI, and XmnI. From previous sequencing of PCR generated products, it was known that there was a HindIII restriction site in the same location as present in the Tth structural gene sequence (corresponding to the same site in the Taq DNA coding sequence). Of the restriction enzymes analyzed, HindIII produced the most convenient products for cloning: a 2050 bp product corresponding to the 3' end of gene and a 3200 bp fragment corresponding to the 5' end of the gene. The two HindIII fragments were cloned as described below.

IV. Cloning Restriction Fragments from the Chromosome

A. HindIII fragment containing the 3' end of the gene

1. Restriction, fractionation, ligation and transformation

TZ05 chromosomal DNA (20 µg) was digested with restriction endonuclease HindIII (200 units) at 37° C. for 18 hours and run over a 1% agarose/1% NuSieve™ GTG agarose gel in TEA, and 500 µl fractions were collected. Selected fractions were concentrated and run on a 0.7% agarose gel. The DNA in this analytical gel was nicked with 0.25N HCl for 15 minutes and transferred to HybondN+™ nylon membrane by capillary action in 0.4N NaOH for 17 hours at room temperature. The DNA was cross-linked to the membrane using the Stratalinker™ 1800 at 50 mjoules. The membranes were treated in prehybridization buffer for 4 hours at 65° C.

2. Preparation of a TZ05 Probe with DG160/DG163 and DG164–DG167

Purified TZ05 PCR fragment generated with DG160–DG163/DG164–DG167 (described above) (1/1000) was amplified with the same primers in a labeling reaction as previously described, extracted with chloroform, desalted over a biogel P-4 spin column, and purified following electrophoresis on a 3% NuSieve™ GTG low melting agarose gel. The fragment was extracted with phenol and then with ether, and concentrated and desalted over a biogel P-4 spin column.

3. Hybridization and autoradiography

The membranes were hybridized with $1.3\times10^6$ CPM of the probe at 65° C. for 18 hours, washed twice in 2×SSPE, 0.1% SDS for 10 minutes at 23° C., and washed in 1×SSPE, 0.1% SDS at 65° C. for 15 minutes, and autoradiographed. The desired fragment was present in two fractions (10 and 11) generated from the electroelufion.

4. Preparation of probe for screening colonies

A fragment previously purified from amplification of TZ05 with DG160–DG163 and DG164–DG167 was used as template (1/1000) in a labeling PCR. The product was extracted with chloroform, desalted over a biogel P-4 spin column, and the fragment was isolated using a 3% NuSieve™ GTG agarose gel. The purified radioactivity labeled fragment was extracted with phenol and then with ether, and desalted over a biogel P-4 spin column.

5. Preparation of vector

Plasmid pBSM13+(8 µg) was digested with HindIII (20 units) at 37° C. for 3 hours, dephosphorylated using bacterial alkaline phosphatase at 37° C. for 45 minutes, extracted with phenol/chloroform and then with ether, and desalted over a biogel P-4 spin column.

6. Cloning the HindIII fragment containing the 3' end of the gene

Fractions collected by electrodution were concentrated and desalted over a biogel P-4 spin column. The fractions were ligated to vector at a 2M excess of insert to vector using T4 DNA ligase at 10° C. for 16 hours, and transformed into DG98. Transformants were seleced on ampicillin-containing agar plates. Colonies were lifted onto nitrocellulose filters, lysed with triton lytic buffer, denatured in 0.5N NaOH, 1M NaCl, neutralized in 0.5M Tris-HCl, pH 8.0, rinsed in 0.3M NaCl, 10 mM Tris, pH 7.6, 1 mM EDTA, and dried and baked at 80° C. for 4 hours. The filters were treated in prghybridization mixture for 2 hours at 65° C.

7. Screening for the HindIII fragment containing the 3' end of the gene

The filters were hybridized with $1.25 \times 10^6$ CPM of probe generated from TZO5 chromosomal DNA with DG160-DG163/DG164-DG167) at 65° C. for 6 days. The filters were washed in 5×SSC, 0.1% SDS at 23° C. for 15 minutes, 2×SSC, 0.1% SDS at 23° C. for 15 minutes, 2×SSC, 0.1% SDS at 60° C. for 15 minutes, and 1×SSC, 0.1% SDS at 60° C. for 15 minutes, and autoradiographed. Probe-positive colonies were inoculated into 10 ml of ampicillin-containing liquid broth and grown at 37° C. for 16 hours.

Plasmid DNA was isolated from 3 ml of each culture by centrifugation, resuspension in 100 μl of 25 mM Tris, 50 mM glucose, 10 mM EDTA, 20 mg/ml lysozyme, pH 8.0, incubation at 23° C. for 14 minutes, lysed by incubation with 200 μl of 2N NaOH, 1% SDS at 23° C. for 11 minutes, and the SDS precipitated by incubation with 150 μl of 3M KOAc, pH 4.8, at 4° C. for 1 hour. Following centrifugation, the supernalant was phenol extracted, ethanol precipitated, and the pellet rinsed with 70% ethanol and resuspended in 50 μl of 10 mM Tris, 0.1 mM EDTA, pH 8, containing 0.2 mg/ml RNaseA.

A portion of the plasmid samples (1/10 volume) was restricted with SmaI and HindIII and a second portion with HindIII alone. The double digest was electrophoresed on a 10% polyacrylamide gel and the single digest electrophoresed on a 1% agarose gel along with radioactively labeled HindIII-digested lambda DNA. Following ethidium staining and photography, all gels were treated with 0.25N HCl for 20 minutes, and transferred to HybondN+™ nylon filter by capillary action in 40 mM NaOH. The DNA was cross-linked to the filter using the Stratalinker™ 1800 set at 50 mjoules, and incubated with prehybridization buffer.

8. Preparation of new probe

A fragment previously purified from amplification of TZ05 chromosomal DNA with DG160-DG163 and DG164-DG167 was used as template (1/100) in a labeling PCR. The product was extracted with chloroform, desalted over a biogel P-4 spin column, and the fragment was isolated using a 3% NuSieve™ GTG agarose gel. The purified radioactively labeled fragment was extracted with phenol and then with ether and desalted over a biogel P-4 spin column.

9. Hybridization of restriction digest blots

The blots were hybridized with $1 \times 10^5$ CPM of probe (generated from TZ05 chromosoma/DNA with DG160-DG163/DG164-DG167) at 65° C. for 72 hours. The membranes were washed twice in 2×SSPE, 0.1% SDS at 23° C. for 10 minutes and once in 1×SSPE, 0.1% SDS at 65° C. for 15 minutes followed, and autoradiographed.

10. Further restriction analysis of clones

Selected clones (2, 5, 7, 11, 15, and 17) were further restricted with SmaI and electrophoresed on a 10% polyacrylamide gel. Following staining and photography, the gel was treated in 0.25N HCl for 30 minutes and transferred to HybondN+™ nylon membrane by capillary action in 40 mM NaOH. The DNA was cross-linked to the membrane using the Stratalinker™ 1800 at 50 mjoules, the membranes treated with prehybridization buffer at 65° C. for 1 hour, and hybridized to probe generated from TZ05 chromosomal DNA with DG160-DG163/DG164-DG167 at 65° C. for 16 hours. The membrane was washed and autoradiographed.

B. HindIII fragment containing the 5' end of the gene

1. Preparation of the membrane fractions

The nitrocellulose membrane (see IV.A.I) containing transferred fractions from the electrophoretic size-separated fractions of TZ05 chromosomal DNA was also used to identify those fractions containing the HindIII fragment encoding the 5' portion of the TZ05 DNA polymerase I gene. The probes were removed from the membrane by boiling in 0.5% SDS.

2. Preparation of a TZ05 probe with DG140/DG141 and MK131

PCR using TZ05 chromosomal DNA amplified using DG168/DG169 and DG136/DG137 was used (1/100) as a template for amplification using DG140/DG141 and MK131 in a labeling reaction. The PCR product was extracted with chloroform, desalted, and the radioactively labeled fragment purified using a 3% NuSieve™ GTG low melting agarose gel.

3. Hybridization and autoradiography

The membranes were hybridized to $1.2 \times 10^6$ CPM at 65° C. for 16 hours, washed twice in 2% SSPE, 0.1% SDS at 23° C. for 10–15 minutes, and 1×SSPE, 0.1% SDS at 23° C. for 14 minutes, and autoradiographed. Given fractions contained the HindIII fragment coding for the 5' end of the gene.

4. Cloning the HindIII fragment containing the 5' end of the gene

The fractions which contained the HindIII fragment coding for the 5' end of the gene were concentrated and desalted over a biogel P-4 spin column. The fractions were ligated to vector at a 2M excess of insert to vector using T4 DNA ligase at 10° C. for 16 hours, transformed into DG98, and transformants selected by plating onto ampicillin-containing media plates. Colonies were lifted onto nitrocellulose filters, lysed with triton lytic buffer, denatured in 0.5N NaOH, 1M NaCl, neutralized in 0.5M Tris-HCl, pH 8.0, rinsed in 0.3M NaCl, 10 mM Tris, pH 7.6, 1 mM EDTA, and dried and baked at 80° C. for 4 hours. The filters were treated with prehybridization mixture for 2 hours at 65° C.

5. Probing for the HindIII fragment containing the 5' end of the gene an screening the clones The filters were hybridized to $1.13 \times 10^6$ CPM of purified probe (generated from TZ05 chromosomal DNA with DG140/DG141 and MK131) at 65° C. for 16 hours, washed with 5×SSC, 0.1% SDS at 23° C. for 17 minutes, 2×SSC, 0.1% SDS at 23° C. for 55 minutes, and autoradiographed. Probe-positive colonies were grown in ampicillin-containing medium.

Plasmid was isolated from 3 ml of each culture by centrifugation, resuspension in 100 μl of 25 mM Tris, 50 mM glucose, 10 mM EDTA, 20 mg/ml lysozyme, pH 8.0, incubation at 23° C. for 11 minutes, lysed by incubation with 200 μl of 2N NaOH, 1% SDS at 23° C. for 10 minutes, and the SDS precipitated by incubation with 150 μl of 3M KOAc, pH 4.8, at 4° C. for 46 minutes. Following centrifugation, the supernatant was phenol extracted, ethanol precipitated, and the pellet rinsed with 70% ethanol and resuspended in 50 μl of 10 mM Tris, 0.1 mM EDTA, pH 8, containing 0.2 mg/ml RNaseA.

A portion of the plasmid samples (1/10 volume) was restricted with XhoI and HindIII and a second portion with HindIII alone. The digests were electrophoresed on a 1% agarose gel along with radioactively labeled HindIII-digested lambda DNA. Following ethidium staining and photography, all gels were treated with 0.25N HCl for 20 minutes, and transferred to HybondN+™ nylon filter by capillary action in 40 mM NaOH. The DNA was cross-linked to the filter using the Stratalinker™ 1800 UV light box set at 50 mjoules, and incubated with prehybridization buffer. These membranes were stored frozen.

6. Confirmation of selected clones by restriction digests

A sample (1/10) of the crude plasmid preparation was restricted with XhoI and EcoRI and electrophoresed on a 1% agarose gel. The gel was treated with 0.25N HCl for 15 minutes and the DNA transferred to HybondN+™ nylon membrane by capillary action using 40 mM NaOH. The DNA was cross-linked to the membrane using the Stratalinker™ 1800 at 50 mjoules and treated with hybridization buffer at 65° C.

7. Preparation of probe

TZ05 chromosomal DNA amplified using DG168/DG169 and DG136/DG137 was used (1/100) as a template for amplification using DG140/DG141 and MK131 in a labeling reaction. The PCR product was extracted with chloroform, desalted over a biogel P-4 spin column, and the fragment was isolated using a 3% NuSieve™ GTG agarose gel. The purified fragment was extracted with phenol and then with ether and desalted over a biogel P-4 spin column.

8. Hyblidization and autoradiography of blots from restriction digests

The membranes (of V.B .6) were hybridized to $5 \times 10^5$ CPM of probe (generated from TZ05 chromosomal DNA with DG152/DG153 and DG148/DG149) at 65° C. for 21 hours. The membranes were washed twice in 2×SSPE, 0.1% SDS at 23° C. for 11 to 15 minutes, and 1×SSPE, 0.1% SDS at 65° C. for 15 minutes, and autoradiographed.

9. Further confirmation by probing restriction blots with a second probe

The previous probe was removed from the blot by boiling the membrane in 0.5% SDS. A second probe of TZ05 chromosomal DNA (10 ng) was made by amplifying with DG157 and DG169 (50 pmoles each), extracting with chloroform, and desalting over a biogel P-4 spin column. The correct product was purified following electrophoresis on a 1% NuSieve™ GTG low melting agarose gel. A fraction of the purified fragment (1/1000) was amplified with DG157 and DG169 under labeling conditions, and the PCR product was extracted with chloroform and purified following electrophoresis on a 3% NuSieve™ GTG low melting agarose gel.

The blots were hybridized with $5 \times 10^5$ CPM of probe at 65° C. for 21 hours, washed twice in 2×SSPE, 0.1% SDS at 23° C. for 11 to 13 minutes, and 1×SSPE, 0.1% SDS at 65° C. for 18 minutes, and autoradiographed. Two orientations were obtained.

10. Isolation of single stranded DNA and plasmid for sequence analysis

Selected clones were grown in methicillin-containing medium to an $OD_{600}$ of 0.2 to 0.3 and infected with R408 helper phage at a MOI of 10. Following growth for 5 hours, the supernatant was collected following centrifugation and the pellets were precipitated with PEG/NaCl. The pellets were resuspended in 10 mM Tris-HCl, 0.1 mM EDTA, pH 8, extracted with phenol, and ethanol precipitated.

The plasmid was isolated as previously described above for screening. The identity of the clones was confirmed following restriction enzyme digestion with EcoRI or ECoRI and HindIII.

11. Sequencing

Selected fragments of the plasmids and single-stranded DNA were sequenced by the dideoxy method. Cultures were first streaked out onto R2-4 plates containing 50 μg/ml of ampicillin, single colonies isolated, and the single-strand DNA isolated as previously described. More single-stranded phage DNA from clones 30 and 31 was isolated, and additional plasmid was isolated as previously described.

C. Summary

Chromosomal DNA was restricted with HindIII, size fractionated by electrophoresis on a 1% agarose, 1% NuSieve™ agarose gel, fractions collected, and the fractions containing the desired size range were concentrated, desalted, and cloned into pBSM13+ (wild type vector from Stratagene). Clones containing the correct sequence were identified by probing with radioactively labeled probes generated from either cloned PCR products or gel purified PCR products. Identity was confirmed by restriction enzyme analysis and by probing of transferred gels with various radioactively labeled PCR products.

D. Sequencing

The DNA sequencing of the structural gene for the TZ05 DNA polymerase gene has been completed and is shown above in the detailed description of the invention. The DNA sequence contains 67% G+C and 33% A+T. There is an 85% DNA identity with Taq polymerase and a 50% identity with *E. coli* polymerase. The derived protein sequence shows 86% identity and 93% homology with the Taq DNA polymerase protein sequence and 39% identity and 58% homology to the *E. coli* DNA polymerase protein sequence. The molecular weight, calculated from the coding sequence, is about 94,065 daltons.

Example 4

Construction of TZ05 Pol Expression Vectors

A number of thermostable Tth DNA polymerase expression vectors are described in the Examples, particularly Example 6, of Ser. No. 455,967, filed Dec. 22, 1989, incorporated herein by reference. These plasmids can be used to place the coding sequence of the TZ05 DNA polymerase gene of the present invention in frame for expression under the control of the lambda $P_L$ promoter.

The expression vectors created are then transformed into *E. coli* K12 strain DG116 and cultured under conditions (see Example 7 of Ser. No. 455,967, incorporated herein by reference) that allow for expression of TZ05 DNA polymerase.

Example 5

PCR With TZ05 DNA Polymerase

About 1.25 units of the TZ05 DNA polymerase purified in Example 1 is used to amplify rRNA sequences from Tth genomic DNA. The reaction volume is 50 μl, and the reaction mixture contains 50 pmol of primer DG73, $10^5$ to $10^6$ copies of the Tth genome ($\sim 2 \times 10^5$ copies of genome/ng DNA), 50 pmol of primer DG74, 200 μM of each dNTP, 2 mM $MgCl_2$, 10 mM Tris-HCl, pH 8.3, 50 mM KCl, and 100 μg/ml gelatin (gelatin may be omitted).

The reaction is carried out on a DNA Thermal Cycler manufactured by Perkin-Elmer (Norwalk, Conn.). Twenty to thirty cycles of 96° C. for 15 seconds; 50° C. for 30 seconds; and 75° C. for 30 seconds are carried out. At 20 cycles, the

47 amplification product (160 bp in size) can be faintly seen on an ethidium bromide stained gel, and at 30 cycles, the product is readily visible (under UV light) on an ethidium bromide stained gel.

The PCR may yield fewer non-specific products if fewer units of TZ05 DNA polymerase are used (i.e., 0.31 units/50 µl reaction). Furthermore, the addition of a non-ionic detergent, such as laureth-12, to the reaction mixture to a final concentration of 1% can improve the yield of PCR product.

Palmers DG73 and DG74 are shown below:

DG73 5'TACGTTCCCGGGCCTTGTAC 3'

DG74 5'AGGAGGTGATCCAACCGCA 3'

We claim:

1. An oligonucleotide in purified form that encodes the amino acid sequence, from amino carboxy terminus:

MetLysAlaMetLeuProLeuPheGluProLysGlyArgValLeu
LeuValAspGlyHisHisLeuAlaTyrArgThrPhePheAlaLeu
LysGlyLeuThrThrSerArgGlyGluProValGlnAlaValTyr
GlyPheAlaLysSerLeuLeuLysAlaLeuLysGluAspGlyTyr
LysAlaValPheValValPheAspAlaLysAlaProSerPheArg
HisGluAlaTyrGluAlaTyrLysAlaGlyArgAlaProThrPro
GluAspPheProArgGlnLeuAlaLeuIleLysGluLeuValAsp
LeuLeuGlyPheThrArgLeuGluValProGlyPheGluAlaAsp
AspValLeuAlaThrLeuAlaLysLysAlaGluArgGluGlyTyr
GluValArgIleLeuThrAlaAspArgAspLeuTyrGlnLeuVal
SerAspArgValAlaValLeuHisProGluGlyHisLeuIleThr
ProGluTrpLeuTrpGluLysTyrGlyLeuLysProGluGlnTrp
ValAspPheArgAlaLeuValGlyAspProSerAspAsnLeuPro
GlyValLysGlyIleGlyGluLysThrAlaLeuLysLeuLeuLys
GluTrpGlySerLeuGluAsnIleLeuLysAsnLeuAspArgVal
LysProGluSerValArgGluArgIleLysAlaHisLeuGluAsp
LeuLysLeuSerLeuGluLeuSerArgValArgSerAspLeuPro
LeuGluValAspPheAlaArgArgArgGluProAspArgGluGly
LeuArgAlaPheLeuGluArgLeuGluPheGlySerLeuLeuHis

48

-continued

GluPheGlyLeuLeuGluAlaProAlaProLeuGluGluAlaPro
TrpProProProGluGlyAlaPheValGlyPheValLeuSerArg
ProGluProMetTrpAlaGluLeuLysAlaLeuAlaAlaCysLys
GluGlyArgValHisArgAlaLysAspProLeuAlaGlyLeuLys
AspLeuLysGluValArgGlyLeuLeuAlaLysAspLeuAlaVal
LeuAlaLeuArgGluGlyLeuAspLeuAlaProSerAspAspPro
MetLeuLeuAlaTyrLeuLeuAspProSerAsnThrThrProGlu
GlyValAlaArgArgTyrGlyGlyGluTrpThrGluAspAlaAla
HisArgAlaLeuLeuAlaGluArgLeuGlnGlnAsnLeuLeuGlu
ArgLeuLysGlyGluGluLysLeuLeuTrpLeuTyrGlnGluVal
GluLysProLeuSerArgValLeuAlaHisMetGluAlaThrGly
ValArgLeuAspValAlaTyrLeuLysAlaLeuSerLeuGluLeu
AlaGluGluIleArgArgLeuGluGluGluValPheArgLeuAla
GlyHisProPheAsnLeuAsnSerArgAspGlnLeuGluArgVal
LeuPheAspGluLeuArgLeuProAlaLeuGlyLysThrGlnLys
ThrGlyLysArgSerThrSerAlaAlaValLeuGluAlaLeuArg
GluAlaHisProIleValGluLysIleLeuGlnHisArgGluLeu
ThrLysLeuLysAsnThrTyrValAspProLeuProGlyLeuVal
HisProArgThrGlyArgLeuHisThrArgPheAsnGlnThrAla
ThrAlaThrGlyArgLeuSerSerSerAspProAsnLeuGlnAsn
IleProIleArgThrProLeuGlyGlnArgIleArgArgAlaPhe
ValAlaGluAlaGlyTrpAlaLeuValAlaLeuAspTyrSerGln
IleGluLeuArgValLeuAlaHisLeuSerGlyAspGluAsnLeu
IleArgValPheGlnGluGlyLysAspIleHisThrGlnThrAla
SerTrpMetPheGlyValSerProGluAlaValAspProLeuMet
ArgArgAlaAlaLysThrValAsnPheGlyValLeuTyrGlyMet
SerAlaHisArgLeuSerGlnGluLeuAlaIleProTyrGluGlu
AlaValAlaPheIleGluArgTyrPheGlnSerPheProLysVal
ArgAlaTrpIleGluLysThrLeuGluGluGlyArgLysArgGly
TyrValGluThrLeuPheGlyArgArgArgTyrValProAspLeu
AsnAlaArgValLysSerValArgGluAlaAlaGluArgMetAla
PheAsnMetProValGlnGlyThrAlaAlaAspLeuMetLysLeu
AlaMetValLysLeuPheProHisLeuArgGluMetGlyAlaArg
MetLeuLeuGlnValHisAspGluLeuLeuLeuGluAlaProGln
AlaArgAlaGluGluValAlaAlaLeuAlaLysGluAlaMetGlu
LysAlaTyrProLeuAlaValProLeuGluValGluValGlyIle
GlyGluAspTrpLeuSerAlaLysGly.

2. An oligonucleotide in purified form that comprises the DNA sequence:

ATGAAGGCGATGCTTCCGCTCTTTGAACCCAAAGGCCGGGTTCTC

CTGGTGGACGGCCACCACCTGGCCTACCGCACCTTCTTCGCCCTA

AAGGGCCTCACCACGAGCCGGGGCGAACCGGTGCAGGCGGTTTAC

GGCTTCGCCAAGAGCCTCCTCAAGGCCCTGAAGGAGGACGGGTAC

AAGGCCGTCTTCGTGGTCTTTGACGCCAAGGCCCCTTCCTTCCGC

CACGAGGCCTACGAGGCCTACAAGGCAGGCCGCGCCCCGACCCCC

GAGGACTTCCCCCGGCAGCTCGCCCTCATCAAGGAGCTGGTGGAC

CTCCTGGGGTTTACTCGCCTCGAGGTTCCGGGCTTTGAGGCGGAC

GACGTCCTCGCCACCCTGGCCAAGAAGGCGGAAAGGGAGGGGTAC

GAGGTGCGCATCCTCACCGCCGACCGGGACCTTTACCAGCTCGTC

TCCGACCGCGTCGCCGTCCTCCACCCCGAGGGCCACCTCATCACC

CCGGAGTGGCTTTGGGAGAAGTACGGCCTTAAGCCGGAGCAGTGG

GTGGACTTCCGCGCCCTCGTGGGGGACCCCTCCGACAACCTCCCC

GGGGTCAAGGGCATCGGGGAGAAGACCGCCCTCAAGCTCCTCAAG

GAGTGGGGAAGCCTGGAAAATATCCTCAAGAACCTGGACCGGGTG

AAGCCGGAAAGCGTCCGGGAAAGGATCAAGGCCCACCTGGAAGAC

CTTAAGCTCTCCTTGGAGCTTTCCCGGGTGCGCTCGGACCTCCCC

CTGGAGGTGGACTTCGCCCGGAGGCGGGAGCCTGACCGGGAAGGG

CTTCGGGCCTTTTTGGAGCGCTTGGAGTTCGGCAGCCTCCTCCAC

-continued

```
GAGTTCGGCCTCCTCGAGGCCCCGCCCCCCTGGAGGAGGCCCCC
TGGCCCCCGCCGGAAGGGGCCTTCGTGGGCTTCGTCCTCTCCCGC
CCCGAGCCCATGTGGGCGGAGCTTAAAGCCCTGGCCGCCTGCAAG
GAGGGCCGGGTGCACCGGGCAAAGGACCCCTTGGCGGGGCTAAAG
GACCTCAAGGAGGTCCGAGGCCTCCTCGCCAAGGACCTCGCCGTT
TTGGCCCTTCGCGAGGGGCTGGACCTCGCGCCTTCGGACGACCCC
ATGCTCCTCGCCTACCTCCTGGACCCCTCCAACACCACCCCCGAG
GGGGTGGCCCGGCGCTACGGGGGGGAGTGGACGGAGGACGCCGCC
CACCGGGCCCTCCTCGCCGAGCGGCTCCAGCAAAACCTCTTGGAA
CGCCTCAAGGGAGAGGAAAAGCTCCTTTGGCTCTACCAAGAGGTG
GAAAAGCCCCTCTCCCGGGTCCTGGCCCACATGGAGGCCACCGGG
GTAAGGCTGGACGTGGCCTATCTAAAGGCCCTTTCCCTGGAGCTT
GCGGAGGAGATTCGCCGCCTCGAGGAGGAGGTCTTCCGCCTGGCG
GGCCACCCCTTCAACCTGAACTCCCGTGACCAGCTAGAGCGGGTG
CTCTTTGACGAGCTTAGGCTTCCCGCCCTGGGCAAGACGCAAAAG
ACGGGGAAGCGCTCCACCAGCGCCGCGGTGCTGGAGGCCCTCAGG
GAGGCCCACCCCATCGTGGAGAAGATCCTCCAGCACCGGGAGCTC
ACCAAGCTCAAGAACACCTACGTGGACCCCCTCCCGGGCCTCGTC
CACCCGAGGACGGGCCGCCTCCACACCCGCTTCAACCAGACAGCC
ACGGCCACGGGAAGGCTCTCTAGCTCCGACCCCAACCTGCAGAAC
ATCCCCATCCGCACCCCCTTGGGCCAGAGGATCCGCCGGGCCTTC
GTGGCCGAGGCGGGATGGGCGTTGGTGGCCCTGGACTATAGCCAG
ATAGAGCTCCGGGTCCTCGCCCACCTCTCCGGGGACGAGAACCTG
ATCAGGGTCTTCCAGGAGGGGAAGGACATCCACACCCAGACCGCA
AGCTGGATGTTCGGCGTCTCCCCGGAGGCCGTGGACCCCCTGATG
CGCCGGGCGGCCAAGACGGTGAACTTCGGCGTCCTCTACGGCATG
TCCGCCCATAGGCTCTCCCAGGAGCTTGCCATCCCCTACGAGGAG
GCGGTGGCCTTTATAGAGCGCTACTTCCAAAAGCTTCCCCAAGGTG
CGGGCCTGGATAGAAAAGACCCTGGAGGAGGGGAGGAAGCGGGGC
TACGTGGAAACCCTCTTCGGAAGAAGGCGCTACGTGCCCGACCTC
AACGCCCGGGTGAAGAGCGTCAGGGAGGCCGCGGAGCGCATGGCC
TTCAACATGCCCGTCCAGGGCACCGCCGCCGACCTCATGAAGCTC
GCCATGGTGAAGCTCTTCCCCCACCTCCGGGAGATGGGGGCCCGC
ATGCTCCTCCAGGTCCACGACGAGCTCCTCCTGGAGGCCCCCCAA
GCGCGGGCCGAGGAGGTGGCGGCTTTGGCCAAGGAGGCCATGGAG
AAGGCCTATCCCCTCGCCGTGCCCCTGGAGGTGGAGGTGGGGATC
GGGAGGACTGGCTTTCCGCCAAGGGC.
```

3. A recombinant DNA vector that comprises the DNA sequence of claim 1.

4. A recombinant host cell transformed with the vector of claim 3.

5. The recombinant host cell of claim 4 that is *E. Coli*.

6. An oligonucleotide in purified form that consists of the DNA sequence:

5'-CAGAACATCCCCATCCGCACCCCCTTGGGCCAGAGGATCCGCCGGGCCTTCG
TGGCCGAGGCGGGATGGGCGTTGGTGGCCCTGGACTATAGCCAGATAGAGCTCC
GGGTCCTCGCCCACCTCTCCGGGGACGAGAACCTGATCAGGGTCTTCCAGGAGG
GGAAGGACATCCACACCCAGACCGCAAGCTGGATGTTCGGCGTCTCCCCGGAGG
CCGTGGACCCCCTGATGCGCCGGGCGGCCAAGACGGTGAACTTCGGCGTCCTCT
ACGGCATGTCCGCCCATAGGCTCTCCCAGGAGCTTGCCATCCCCTACGAGGAGG
CGGTGGCCTTTATAGAGCGCTACTTCCAAAGCTTCCCCAAGGTGCGGGCCTGGA
TAGAAAAGACCCTGGAGGAGGGGAGGAAGCGGGGCTACGTGGAAACC.

7. An oligonucleotide in purified form that consists of the DNA sequence:

5'-GCCCACATGGAGGCCACCGGGGTAAGGCTGGACGTGGCCTATCTAAAGG

CCCTTTCCCTGGAGCTTGCGGAGGAGATTCGCCGCCTCGAGGAGGAGGTCT

TCCGCCTGGCGGGCCACCCCTTCAACCTGAACTCCCGTGACCAGCTAGAGC

GGGTGCTCTTTGACGAGCTTAGGCTTCCCGCCCTGGGCAAGACGCAAAAGA

CGGGGAAGCGCTCCACCAGCGCCGCGGTGCTGGAGGCCCTCAGGGAGGCCC

ACCCCATCGTGGAGAAGATCCTCCAGCACCGGGAGCTCACCAAGCTCAAGA

ACACCTACGTGGACCCCCTCCCGGGCCTCGTCCACCCGAGGACGGGCCGCC

TCCACACCCGCTTCAACCAGACAGCCACGGCCACGGGAAGGCTCTCTAGCT

CCGACCCCAACCTGCAGAACATCCCCATCCGCACCCCCTTGGGCCAGAGGA

TCCGCCGGGCCTTCGTGGCCGAGGCGGGATGGGCGTTGGTGGCCCTGGACT

ATAGCCAGATAGAGCTCCGGGTCCTCGCCCACCTCTCCGGGGACGAGAACC

TGATCAGG.

8. An oligonucleotide in purified form that encodes the amino acid sequence consisting of, from amino carboxy terminus:

GlnAsnIleProIleArgThrProLeuGlyGlnArgIleArgArg

AlaPheValAlaGluAlaGlyTrpAlaLeuValAlaLeuAspTyr

SerGlnIleGluLeuArgValLeuAlaHisLeuSerGlyAspGlu

AsnLeuIleArgValPheGlnGluGlyLysAspIleHisThrGln

ThrAlaSerTrpMetPheGlyValSerProGluAlaValAspPro

LeuMetArgArgAlaAlaLysThrValAsnPheGlyValLeuTyr

GlyMetSerAlaHisArgLeuSerGlnGluLeuAlaIleProTyr

GluGluAlaValAlaPheIleGluArgTyrPheGlnSerPhePro

LysValArgAlaTrpIleGluLysThrLeuGluGluGlyArgLys

ArgGlyTyrValGluThr.

9. An oligonucleotide in purified form that encodes the amino acid sequence consisting of, from amino carboxy terminus:

AlaHisMetGluAlaThrGlyValArgLeuAspValAlaTyrLeu

LysAlaLeuSerLeuGluLeuAlaGluGluIleArgArgLeuGlu

GluGluValPheArgLeuAlaGlyHisProPheAsnLeuAsnSer

ArgAspGlnLeuGluArgValLeuPheAspGluLeuArgLeuPro

AlaLeuGlyLysThrGlnLysThrGlyLysArgSerThrSerAla

AlaValLeuGluAlaLeuArgGluAlaHisProIleValGluLys

-continued

IleLeuGlnHisArgGluLeuThrLysLeuLysAsnThrTyrVal

AspProLeuProGlyLeuValHisProArgThrGlyArgLeuHis

ThrArgPheAsnGlnThrAlaThrAlaThrGlyArgLeuSerSer

SerAspProAsnLeuGlnAsnIleProIleArgThrProLeuGly

GlnArgIleArgArgAlaPheValAlaGluAlaGlyTrpAlaLeu

ValAlaLeuAspTyrSerGlnIleGluLeuArgValLeuAlaHis

LeuSerGlyAspGluAsnLeuIleArg.

10. A recombinant DNA vector that comprises a DNA sequence, which DNA sequence consists of the DNA sequence of claim 6.

11. A recombinant DNA vector that comprises a DNA sequence, which DNA sequence consists of the DNA sequence of claim 7.

12. A recombinant DNA vector that comprises a DNA sequence, which DNA sequence consists of the DNA sequence of claim 8.

13. A recombinant DNA vector that comprises a DNA sequence, which DNA sequence consists of the DNA sequence of claim 9.

14. A recombinant host cell transformed with the vector of claim 10.

15. A recombinant host cell transformed with the vector of claim 11.

16. A recombinant host cell transformed with the vector of claim 12.

17. A recombinant host cell transformed with the vector of claim 13.

* * * * *